United States Patent
Reith et al.

(10) Patent No.: US 12,263,278 B2
(45) Date of Patent: Apr. 1, 2025

(54) ADDITIVELY MANUFACTURED POROUS POLYMER MEDICAL IMPLANTS

(71) Applicant: Curiteva, Inc., Tanner, AL (US)

(72) Inventors: Todd Reith, West Chester, PA (US); Erik Erbe, Manchester, MO (US); Eric Linder, Dublin, OH (US); Ryan Heskett, Wellington, FL (US)

(73) Assignee: Curiteva, Inc., Tanner, AL (US)

( * ) Notice: Subject to any disclaimer, the term of this patent is extended or adjusted under 35 U.S.C. 154(b) by 51 days.

(21) Appl. No.: 18/132,048

(22) Filed: Apr. 7, 2023

(65) Prior Publication Data

US 2023/0321324 A1    Oct. 12, 2023

Related U.S. Application Data

(60) Provisional application No. 63/429,746, filed on Dec. 2, 2022, provisional application No. 63/329,209, filed on Apr. 8, 2022.

(51) Int. Cl.
*A61L 27/56* (2006.01)
*A61L 27/18* (2006.01)
*A61F 2/30* (2006.01)

(52) U.S. Cl.
CPC .............. *A61L 27/56* (2013.01); *A61L 27/18* (2013.01); *A61F 2002/30784* (2013.01);
(Continued)

(58) Field of Classification Search
CPC .................... A61L 27/56; A61L 27/18; A61F 2002/30784; A61F 2002/30838;
(Continued)

(56) References Cited

U.S. PATENT DOCUMENTS 9,066,815 B2   6/2015   Garber
9,193,110 B2   11/2015  Pridoehl et al.
(Continued)

FOREIGN PATENT DOCUMENTS

CN   108215194   6/2018
CN   112941656   6/2021
(Continued)

OTHER PUBLICATIONS

International Search Report and Written Opinion in International Appln. No. PCT/US2023/017842, dated Jul. 18, 2023, 11 pages.
(Continued)

*Primary Examiner* — Yashita Sharma
(74) *Attorney, Agent, or Firm* — Fish & Richardson P.C.

(57) ABSTRACT

An article includes multiple layers of polyaryletherketone (PAEK), in which each layer is composed of a continuous length of PAEK, in which the continuous length of PAEK in at least one of the layers includes an interior portion, and an exterior surface including crystalline regions, in which a crystallinity of the exterior surface is higher than a crystallinity of the interior portion. The cross-sectional area of the continuous length of PAEK is non-uniform within each layer. Each layer defines a plane, and a portion of the continuous length of PAEK in each layer extends out of the plane defined by the layer. The multiple layers of PAEK define a network of interconnected pores.

30 Claims, 32 Drawing Sheets
(16 of 32 Drawing Sheet(s) Filed in Color)

(52) U.S. Cl.
CPC .............. *A61F 2002/30838* (2013.01); *A61F 2002/3092* (2013.01); *A61F 2002/3093* (2013.01); *A61F 2002/30971* (2013.01); *A61F 2002/30985* (2013.01)

(58) Field of Classification Search
CPC ...... A61F 2002/3092; A61F 2002/3093; A61F 2002/30971; A61F 2002/30985
See application file for complete search history.

(56) References Cited

U.S. PATENT DOCUMENTS

| | | | |
|---|---|---|---|
| 9,250,620 | B2 | 2/2016 | Kotlus |
| 9,433,969 | B2 | 9/2016 | Pridoehl et al. |
| 9,527,242 | B2 | 12/2016 | Rodgers et al. |
| 9,925,714 | B2 | 3/2018 | Rodgers et al. |
| 10,189,210 | B2 | 1/2019 | Rodgers et al. |
| 10,335,856 | B2 | 7/2019 | Swaminathan et al. |
| 10,350,824 | B2 | 7/2019 | Ng et al. |
| 10,350,876 | B2 | 7/2019 | Ng et al. |
| 10,562,227 | B2 | 2/2020 | Go et al. |
| 10,596,660 | B2 | 3/2020 | McCarthy et al. |
| 10,875,244 | B2 | 12/2020 | Montgomery |
| 11,135,771 | B1 | 10/2021 | Reith et al. |
| 11,481,886 | B1 | 10/2022 | Reith et al. |
| 2006/0052880 | A1 | 3/2006 | Brosnahan et al. |
| 2006/0249875 | A1* | 11/2006 | Robb ............... B33Y 50/00 264/239 |
| 2013/0327917 | A1 | 12/2013 | Steiner et al. |
| 2014/0134335 | A1 | 5/2014 | Pridoehl et al. |
| 2014/0277461 | A1* | 9/2014 | Nebosky ............. A61F 2/442 156/60 |
| 2015/0028523 | A1 | 1/2015 | Jaker et al. |
| 2015/0112438 | A1 | 4/2015 | McLean |
| 2016/0096326 | A1 | 4/2016 | Naware |
| 2016/0220726 | A1* | 8/2016 | Nies .................. A61L 27/02 |
| 2016/0339633 | A1 | 11/2016 | Stolyarov et al. |
| 2017/0120334 | A1 | 5/2017 | DeMuth |
| 2017/0128601 | A1 | 5/2017 | DeCiccio et al. |
| 2017/0165908 | A1 | 6/2017 | Pattinson et al. |
| 2017/0173877 | A1 | 6/2017 | Myerberg et al. |
| 2018/0028321 | A1* | 2/2018 | Zhu .................. A61L 27/28 |
| 2018/0085826 | A1 | 3/2018 | Luo |
| 2018/0200955 | A1 | 7/2018 | Walter et al. |
| 2018/0263785 | A1 | 9/2018 | Vishnubhotla et al. |
| 2019/0030806 | A1 | 1/2019 | Herman et al. |
| 2019/0209354 | A1* | 7/2019 | Scanlon ............. A61F 2/915 |
| 2020/0086254 | A1 | 3/2020 | Rodriguez |
| 2022/0324170 | A1 | 10/2022 | Reith et al. |
| 2022/0327679 | A1 | 10/2022 | Reith et al. |

FOREIGN PATENT DOCUMENTS

| | | |
|---|---|---|
| CN | 114479064 | 5/2022 |
| EP | 3436503 | 2/2020 |
| FR | 3119791 | 8/2022 |
| WO | WO 2019/068581 | 4/2019 |

OTHER PUBLICATIONS

Artstor, "3D Printed PEEK Bone Foam," Artstor, University of Pennsylvania Fisher Fine Arts Library Material Collection, retrieved from URL<https://library.artstor.org/#/public/27529254>, retrieved on May 4, 2021, 2 pages.

Artstor, "3D Printed PEEK Bone Mesh," Artstor, University of Pennsylvania Fisher Fine Arts Library Material Collection, retrieved from URL<https://library.artstor.org/#/public/27529255>, retrieved May 4, 2021, 2 pages.

Bhatnagar et al., "High performance ballistic fibers and tapes," 2016, Lightweight Ballistic Composites, No. 2, 10 pages.

Biomaterials for Implant Applications, "VESTAKEEP® PEEK," Evonik Industries, Jan. 14, 2020, pp. 1-16.

Braun, "Cervical interbody fusion cage; CeSPACE® 3D," Aesculap®—anterior/ 3D-printed, retrieved from URL<https://www.medicalexpo_com/prod/aesculap/product-70641-957836.html>, retrieved on Mar. 22, 2021, 5 pages.

Chen et al., "Porous Scaffold Design for Additive Manufacturing in Orthopedics: A Review," Frontiers in Bioengineering and Biotechnology, Jun. 2020, vol. 8, pp. 1-19.

Evonik, "PEEK for medical applications; VESTAKEEP®; Evonik Industries AG," Sep. 2013, retrieved from URL<https://www.modernplastics.com/wp-content/uploads/2015/09/Evonik-VESTAKEEP-PEEK-medical-Flyer-MODERN-Plastics-WEB-4pages.pdf>, pp. 1-4.

Evonik, "The World's first implant grade PEEK Filament for Additive Manufacturing," Vestakeep 3DF PEEK Filament, Corporate Presentation, 2019.

FossiLabs, "Bone Foam Images," previously accessible on https://www.fossilabs.com, 2019-2020, 3 pages.

FossiLabs, "Bone Foam, Bone Mesh, Wedge Images," FossiLabs, previously accessible on <https://www.fossilabs.com>, 2019-2020, 7 pages.

FossiLabs, "FossilLabs Offers 3D Printed 'Fully' Porous PEEK Bone-Like Scaffolding Structures," Fossilabs, LLC, Jan. 1, 2020, retrieved from URL<https://fossilabs.com/pub/Fossilabs_PR_01012020.pdf>, 1 page.

FossiLabs, Screenshots from Fossilabs Website, previously accessible on <https://www.fossilabs.com>, 2019-2020, 3 pages.

International Search Report and Written Opinion in International Appln. No. PCT/US2021/052651, dated Jan. 19, 2022, 15 pages.

Koci, "Everything you need to know about infills," Prusa Printers, Jan. 2021, 35 pages.

ManufacturingTechInsights.com, "Top 10 3D Printing Solution Providers—2020," Manufacturing Technology Insights; ISSN 2644-2493 Mar. 6, 2020, retrieved from URL<https://3d-printing_manufacturingtechnologyinsights.com/vendors/top-3d-printing-solution-companies-2020_html>, pp. 1-2.

Mattox, Film Characterization and Some Basic Film Properties, 2010, Handbook of Physical Vapor Deposition (PVD) Processing, Second Edition, all.

Palermo, "Fused Deposition Modeling: Most Common 3D Printing Method," 2013, Live Science, 13 pages.

Saad et al., The fatigue behavior of composite materials for high temperature applications, 2016, Lightweight Composite Structures in Transport, p. 1 (Year: 2016) (abstract only).

VESTAKEEP, "Additive Manufacturing Biomaterials for Permanent Implants," MOS Annual Meeting, Evonik Promotional Material, VESTAKEEP®, Mar. 13-15, 2019, 1 page.

Zheng et al., "Effects of printing path and material components on mechanical properties of 3D-printed polyether-ether-ketone/hydroxyapatite composites," Journal of Mechanical Behavior of Biomedical Materials, 2021, 118, 9 pages.

De Oliveira et al., "Influence of Nano-Hydroxyapatite Coating Implants on Gene Expression of Osteogenic Markers and Micro-CT Parameters. An in Vivo Study in Diabetic Rats," Society for Biomaterials, Jun. 2020, 13 pages.

Evonik, "Vestakeep Peek: Biomaterials for Implant Applications," available on or before Jan. 2021, 16 pages.

FossiLabs, "Porous Bone-Like Scaffolding," available before Apr. 8, 2022, Corporate presentation, 7 pages.

Promimic, "HAnano Surface Research Monograph," Jul. 2023, 19 pages.

Scombatti de Souza et al., "Microtomographic Evaluation of a New Nanometric Hydroxyapatite Covered Implant Surface. In Vivo Study in Diabetic Rats," Slin. Oral Impl. Res., 2016, 1 page.

* cited by examiner

ADDITIVELY MANUFACTURED POROUS POLYMER MEDICAL IMPLANTS

CLAIM OF PRIORITY

This application claims priority to U.S. Patent Application Ser. No. 63/429,746, filed on Dec. 2, 2022, and to U.S. Patent Application Ser. No. 63/329,209, filed on Apr. 8, 2022, the contents of both of which are incorporated here by reference in their entirety.

BACKGROUND

Medical implants are devices that are placed into the body to replace or support a biological structure, such as bone.

SUMMARY

In a first aspect, an article including multiple layers of polyaryletherketone (PAEK), in which each layer is composed of a continuous length of PAEK, in which the continuous length of PAEK in at least one of the layers includes: an interior portion, and an exterior surface including crystalline regions, in which a crystallinity of the exterior surface is higher than a crystallinity of the interior portion. The cross-sectional area of the continuous length of PAEK is non-uniform within each layer, or each layer defines a plane and a portion of the continuous length of PAEK in each layer extends out of the plane defined by the layer, or both. The multiple layers of PAEK define a network of interconnected pores.

Embodiments can include one or any combination of two or more of the following features.

The continuous length of PAEK in each layer is disposed in aligned rows. In some cases, the rows have a serpentine, curved, or zig-zag configuration. In some cases, the rows in each layer are rotated relative to the rows in an adjacent layer. In some cases, the rows in each layer are rotated by between 20-60° relative to the rows in the adjacent layer. In some cases, the rows in each layer are rotated by 36° relative to the rows in the adjacent layer.

The cross sectional area of the continuous length of PAEK is non-uniform within each layer.

The continuous length of PAEK is extends between adjacent layers.

Each layer defines a plane, and in which a portion of the continuous length of PAEK in each layer extends out of the plane defined by the layer.

The continuous length of PAEK in each layer intersects the continuous length of PAEK in an adjacent layer at nodes. In some cases, the continuous length of PAEK extending between adjacent nodes is non-linear.

The exterior surface of the continuous length of PAAK includes crystalline domains separated by amorphous regions.

The exterior surface of the continuous length of PAEK includes a lamellar surface microstructure. In some cases, the lamellar surface microstructure has a characteristic dimension of between 4-6 nm. In some cases, the lamellar surface microstructure forms spherules on the exterior surface of the continuous length of PAEK. In some cases, the spherules have a characteristic dimension of 4-6 µm.

The continuous length of PAEK in a first set layers of the multiple layers has a crystallinity that differs from the continuous length of PAEK in a second set of the layers of the multiple layers.

The multiple layers of PAEK define a trabecular structure.

The multiple layers of PAEK form a triply periodic minimal surface (TPMS) structure defining the network of interconnected pores. In some cases, the multiple layers of PAEK form a TPMS diamond structure.

A surface roughness of the continuous length of PAEK is between 0.5 µm and 3.0 µm, e.g., between 1 µm and 1.5 µm.

A Young's modulus of elasticity of the article is between 0.3 GPa and 4.0 GPa, e.g., between 0.8 GPa and 1.5 GPa.

A compression strength of the article is at least 20 kN, e.g., between 20 kN and 150 kN, between 20 kN and 100 kN, or between 20 kN and 30 kN.

A fatigue strength of the article is between 1200 N and 1800 N measured over 5 M cycles at 5 Hz.

A stiffness of the article is between 0.8 GPa and 1.5 GPa.

The article includes a coating including hydroxyapatite disposed on the exterior surface of the continuous length of PAEK. In some cases, the coating has a thickness of between 1 nm and 80 nm, e.g., between 1 nm and 50 nm or between 1 nm and 20 nm.

The continuous length of PAEK has between 20% and 60% crystallinity by volume, e.g., between 30% and 50% crystallinity by volume.

The article has a porosity of between 40-80%.

The pores have dimensions between 100 µm-1 mm, e.g., between 100 µm and 700 µm.

An average dimension of the pores is between 220-280 µm.

The PAEK includes polyetheretherketone (PEEK).

The multiple layers of PAEK define a first region having a first porosity and a second region having a second porosity different from the first porosity, in which both the first region and the second region span at least some of the multiple layers. In some cases, the continuous length of PAEK extends between the first region and the second region.

The continuous length of PAEK is deposited by additive manufacturing, such as fused strand fabrication.

The article includes a medical implant. In some cases, the medical implant is osteoconductive. In some cases, the medical implant is osteointegrative. In some cases, the medical implant is osteogenic.

In a second aspect, combinable with the first aspect, a medical implant includes multiple layers of PAEK deposited by fused strand fabrication, in which each layer is composed of a continuous length of PAEK disposed in aligned rows, and in which the continuous length of PAEK extends between adjacent layers, in which the continuous length of PAEK in at least one of the layers includes: an interior portion, and an exterior surface including crystalline regions, in which a crystallinity of the exterior surface is higher than a crystallinity of the interior portion, and the cross-sectional area of the continuous length of PAEK is non-uniform within each row; in which the rows in each layer are rotated relative to the rows in each adjacent layer to form a TPMS diamond structure defining a network of interconnected pores such that a porosity of the medical implant is between 50-70%, and in which the medical implant is osteoconductive.

Embodiments can include one or any combination of two or more of the following features.

The medical implant includes a cervical implant.

The medical implant includes a posterior lumbar interbody fusion implant, a transforaminal lumbar interbody fusion implant, an anterior lumbar interbody fusion implant, or a direct lateral interbody fusion implant.

The medical implant includes a joint implant.

In a third aspect, combinable with the first and second aspects, a medical implant is produced by a process including: extruding a filament of PAEK from a nozzle of an additive manufacturing tool to deposit each of multiple layers of PAEK, in which each layer is composed of a continuous length of PAEK; and annealing the deposited multiple layers to induce crystallization of regions of an exterior surface of the continuous length of PAEK, in which a crystallinity of the exterior surface is higher than a crystallinity of an interior portion of the continuous length of PAEK, in which the multiple layers of PAEK define a network of interconnected pores.

Embodiments can include one or any combination of two or more of the following features.

Extruding the filament of PAEK includes forming aligned rows of the continuous length of PAEK in each layer.

The process includes continuously extruding the filament of PAEK to form adjacent layers such that the continuous length of PAEK extends between the adjacent layers.

The process includes extruding the filament of PAEK such that each layer defines a plane, and such that a portion of the continuous length of PAEK extends out of the plane defined by the layer.

The process includes extruding the filament of PAEK such that the continuous length of PAEK in each layer intersects that continuous length of PAEK in an adjacent layer at nodes. In some cases, the continuous length of PAEK extending between adjacent nodes is non-linear.

The process includes extruding the filament of PAEK such that the continuous length of PAEK has a non-uniform cross-sectional area within each layer.

The process includes extruding the filament of PAEK such that the multiple layers form a triply periodic minimal surface (TPMS) structure defining the network of interconnected pores. In some cases, the multiple layers form a TPMS diamond structure.

The process includes rotating the additive manufacturing tool after depositing each layer of PAEK. In some cases, the process includes rotating the additive manufacturing tool by between 20-60° after depositing each layer.

The process includes heating the nozzle of the manufacturing tool to a temperature of between 325-475° C., e.g., to a temperature of between 400-450° C.

Extruding the filament of PAEK includes depositing a first one of the layers onto a heated platform.

The process includes extruding the filament of PAEK at an extrusion flow rate of between 10-15 mm/s.

The process includes moving the nozzle relative to the deposited layers at a feed rate of between 5-15 mm/s.

The process includes extruding the filament of PAEK at an extrusion ratio of between 0.5-4.0, in which the extrusion ratio is the ratio between an extrusion flow rate of the PAEK to a rate of motion of the nozzle relative to the deposited layers. In some cases, the filament of PAEK is extruded at an extrusion ratio of between 0.5-2.0, e.g., at an extrusion ratio of between 0.6-1.0.

The process includes annealing the deposited multiple layers at a temperature below a glass transition temperature of the PAEK. In some cases, annealing the deposited multiple layers includes forming a lamellar surface microstructure on the exterior surface of the continuous length of PAEK.

The process includes disposing a coating including hydroxyapatite onto the exterior surface of the continuous length of PAEK. In some cases, disposing the coating includes disposing the coating by dip coating, immersion coating, or spray coating.

The process includes extruding the filament of PAEK using a fused strand deposition process.

The process includes extruding the filament of PAEK using a fused filament fabrication process.

The process includes extruding the filament of PAEK using a fused melt deposition process.

The process includes extruding the filament of PAEK to form a first region having a first porosity and a second region having a second porosity different from the first porosity, in which both the first region and the second region span at least some of the multiple layers. In some cases, the continuous length of PAEK extends between the first region and the second region.

The approaches described here can have one or more of the following advantages. The porous PAEK medical implants described here have mechanical properties, such as strength and modulus, that are comparable to those of physiologic bone. Moreover, the porous PAEK medical implants described here are bioactive, exhibiting osteogenic behavior (e.g., osteoconduction, osseointegration, and immunomodulation (osteoinduction)). Porous PAEK medical implants with this combination of mechanical and biological properties facilitate rapid and durable bone growth when implanted into a subject.

The details of one or more implementations are set forth in the accompanying drawings and the description below. Other features and advantages will be apparent from the description and drawings, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

We describe here medical implants formed by additive manufacturing of polyaryletherketone (PAEK), e.g., by fused strand deposition of PAEK. The resulting medical implants have a sparse lattice structure defining a network of interconnected pores and that mimics the structure of physiologic (e.g., trabecular) bone. The PAEK strands of the implant have a semi-amorphous interior and an exterior surface that has crystalline domains that provide a surface roughness that also mimics the physiologic environment. The PAEK strands in the implant are non-uniform in cross-sectional area and are non-linear, e.g., such that the PAEK strands in one layer have an attenuated profile that extends into the underlying layer.

These porous PAEK medical implants exhibit mechanical properties, such as strength and modulus, that are comparable or better than the mechanical properties of physiologic bone. Moreover, these porous PAEK medical implants are biologically active, exhibiting osteoconductive, osseointegrative, osteogenic, and immunomodulatory behavior.

Figure 1:
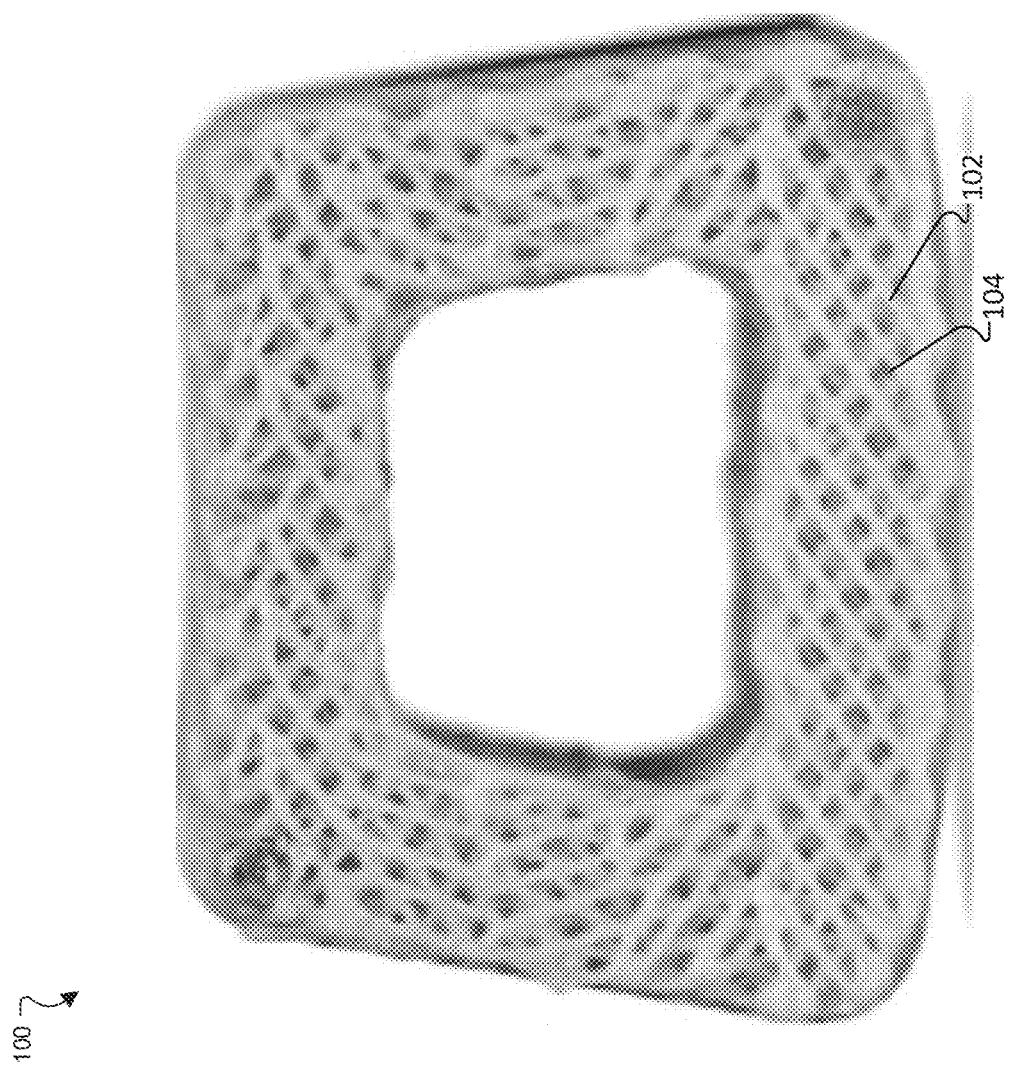
FIG. 1 is a photograph of a porous PAEK medical implant.

Referring to FIG. 1, a medical implant 100 is a porous structure formed of multiple additively manufactured layers of a polyaryletherketone (PAEK) thermoplastic, such as polyetherketone (PEK), polyetheretherketone (PEEK), polyetherketoneketone (PEKK), polyetheretherketoneketone (PEEKK), or polyetherketoneetherketoneketone (PEKEKK). Each layer of PAEK is composed of one or more continuous lengths of PAEK. A continuous length of PAEK is a strand of PAEK that is deposited by continuous (e.g., without interruption) extrusion of PAEK from an additive manufacturing tool. In the example of FIG. 1, the one or more continuous lengths of PAEK in each layer are disposed in aligned rows 102 (see also FIGS. 2A-2B); however, in some examples the continuous length of PAEK is disposed in other configurations. The continuous lengths of PAEK define a network of interconnected pores 104. The medical implant 100 of FIG. 1 is a cervical implant; however, other types of bone implants can have similar structure and composition.

The medical implant 100 is has osteogenic potential. For instance, the medical implant is osteoconductive, e.g., bone cells can grow on the surface of the medical implant. The medical implant 100 is also osseointegrative, meaning that a direct structural connection can be formed between bone and the implant 100, e.g., a connection that cannot be separated without fracture. In addition, the medical implant 100 is immunomodulative (e.g., having osteoinductive potential), meaning that the medical implant is able to induce osteogenesis, e.g., by recruiting immature cells and stimulating those cells to develop into preosteoblasts. For instance, within a period of about 4-12 weeks after implantation into a live subject, substantially all (e.g., greater than 90% or greater than 95%) of the pore volume of the medical implant 100 is filled with viable, natural bone. Without being bound by theory, it is believed that the surface microstructure, pore structure, and composition of the medical implant contributes to the osteogenic (e.g., osteoconductive, osseointegrative, and immunomodulatory/osteoinductive) behavior of the medical implant 100, as discussed in more detail below.

Osseointegration can be characterized in various ways, including by histologic bone apposition and histologic bone quality, physiologic bone quality, biomechanical bone quality, the quality of the bone-implant interface, and the persistence (e.g., longevity) of the bone. Osteoinduction (e.g., immunomodulation) can be characterized by a macrophage polarization array indicative of regenerative behavior, e.g., by muscle pouch implantation. Osteogenesis can be characterized by cell differentiation and gene expression.

The porous PAEK medical implants described here have a substantially periodic lattice structure that defines a network of interconnected pores, as discussed below. This structure gives the medical implant a high compressive strength, elastic modulus, and toughness. The interconnected nature of the pores, as well as the pore size distribution, contributes to the osteogenic behavior of the medical implant.

The surface microstructure of the porous PAEK medical implants described here contributes to their physiologic behavior. For instance, the surface crystallinity and surface roughness that is achieved by the fused strand deposition fabrication process toughens the PAEK and renders the surface hydrophilic, mimicking physiologic biomechanics and encouraging osteogenesis. The surface microstructure, e.g., the nano-textured crystallinity of the surface, also mimics physiologic bone and contributes to osteogenic behavior (e.g., osteoconduction, osseointegration, and immunomodulation (e.g., osteoinduction).

Figure 2A:
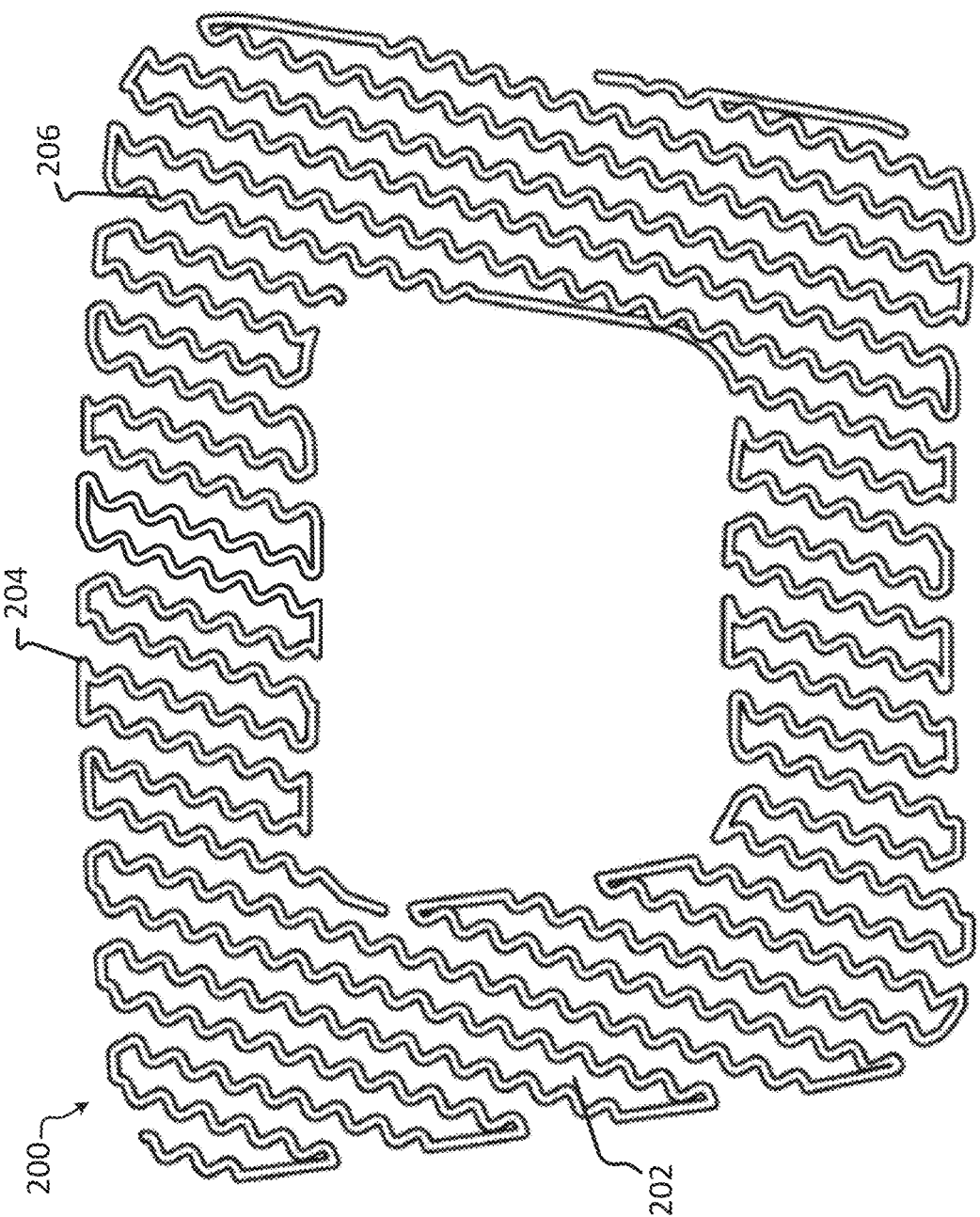
FIGS. 2A and 2B are diagrams of layers of a porous PAEK medical implant.

FIG. 2A is a schematic depiction of a single layer 200 of a porous PAEK medical implant. The layer 200 is composed of two continuous lengths of PAEK 202, 204 that are disposed in aligned rows 206, with each continuous length of PAEK 202, 204 extending between adjacent rows. In some examples, each layer of a medical implant is composed of a single continuous length of PEEK, and in some examples, each layer of a medical implant includes multiple continuous lengths of PEEK.

The rows 206 are spaced apart such that the layer 200 is sparsely filled with material, e.g., such that less than 50% of the total area of the layer is occupied by PAEK material, e.g., less than 30% or less than 25%. For instance, the PAEK material of each row has a width $w_r$ of between 75 μm and 400 μm, and adjacent rows are separated by a gap having a width $w_g$ of between 50 μm and 500 μm. The rows 202 of the layer 200 of FIG. 2A have a serpentine configuration, but in some examples, the rows have other configurations, such as a zig-zag, curved, sinusoidal, or straight-line configuration. In some examples, the one or more continuous lengths of PAEK in the layer 200 are randomly arranged.

Figure 2B:
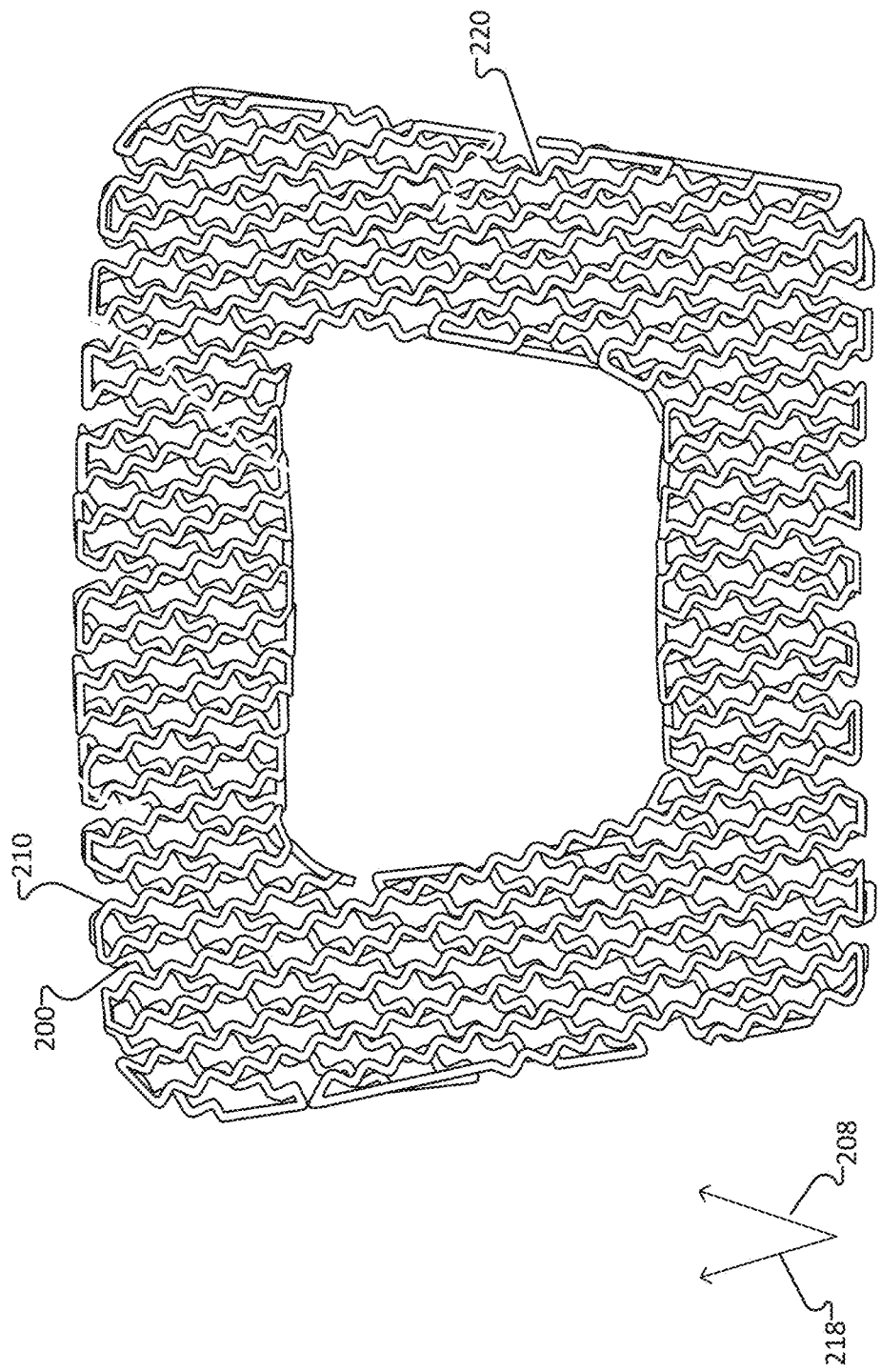

The porous PAEK medical implant includes multiple layers stacked on top of one another. FIG. 2B shows the layer 200 of FIG. 2A, with a second layer 210 disposed on top of the layer 200. Each layer 200, 210 is composed of one or more continuous lengths of PAEK, e.g., arranged in aligned rows, as discussed with respect to FIG. 2A. In some examples, a continuous length of PAEK extends between adjacent layers 200, 210, thereby connecting the two layers. Subsequent layers can be structured similarly, such that a continuous length of PAEK extends between at least some pairs of adjacent layers in the medical implant.

The direction of the rows of each layer define an orientation of the layer. In the medical implant, the orientation of each layer differs from the orientation of the adjacent layer, e.g., the rows of one layer are rotated relative to the rows of each adjacent layer. The orientation of the layers 200, 210 are indicated by arrows 208, 218, respectively. In general, the rows of one layer of a medical implant are rotated by between 20° and 60°, e.g., between 20° and 40° or between 30° and 40°, e.g., about 36°, relative to the rows of the adjacent layer. In the example of FIG. 2A, the rows of the layer 200 are rotated by about 30° relative to the rows of the layer 210.

The continuous length of PAEK in each layer (e.g., in the layer 200) contacts the continuous length of PAEK in the adjacent layer (e.g., in the layer 210) at nodes, e.g., node 220. The PAEK in the overlying layer 210 is supported by the PAEK in the underlying layer 200 at the nodes 220, but the portions of the continuous length of PAEK that extend between adjacent nodes are unsupported by the underlying layer. Because of sparse structure and the relative rotations of the layers, and due to the time and temperature profile of the fabrication process, discussed further below, at least some of the unsupported portions of the continuous length of PAEK in a given layer droop out of the plane defined by that layer and towards the plane defined by the underlying layer, e.g., defining a non-linear connection between the nodes. For instance, the unsupported portions of PAEK that droop from one layer into an underlying layer extend into the plane of the underlying layer by an amount up to about 50% of the height of the underlying layer, e.g., between 10% and 30% or between 25% and 50%. In a specific example, when the layers 200, 210 each has a height of about 200 μm, the unsupported portions of PAEK from the overlying layer 210 extend into the plane of the underlying layer by between 75 μm and 100 μm.

The time and temperature profile of the fabrication process also causes the continuous length of PAEK to have a non-uniform cross-sectional diameter or cross-sectional area within each layer. For instance, the continuous length of PAEK at or near the nodes can have a diameter or cross-sectional area that is larger than the diameter or cross-sectional area of the same continuous length of PAEK in the portion extending between nodes. In examples, the cross-sectional area at the narrowest portion of the attenuated length of PAEK (e.g., near the midpoint between the nodes) is between 10% and 50% less than the cross-sectional area at the widest portion (e.g., at or near the nodes), e.g., between 20% and 40%, between 10% and 25%, or between 25% and 50%.

In some examples, one or more of the continuous lengths of PAEK in the medical implant extend between adjacent nodes, e.g., the extrusion of PAEK is interrupted at each node. In some examples, one or more of the continuous lengths of PAEK extend across multiple nodes, e.g., some or all of the nodes in each row of a given layer. In some examples, one or more of the continuous lengths of PAEK extend across multiple rows (e.g., as illustrated in FIG. 2A). The continuous lengths of PAEK in a given medical implant can all have the same length or can be of different lengths.

Figure 3B:
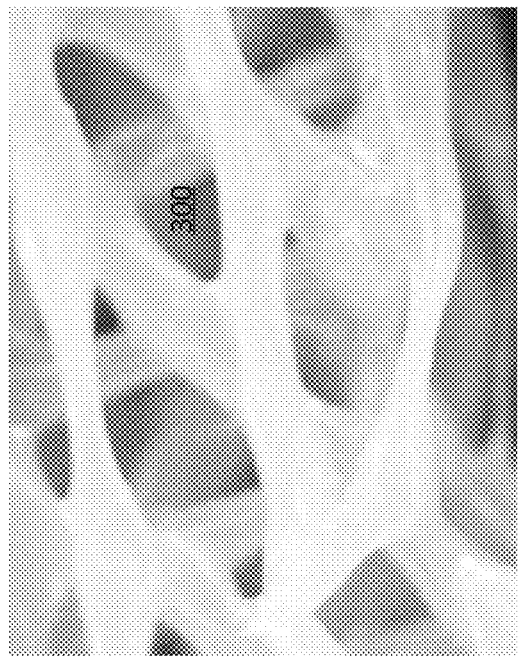
FIGS. 3A and 3B are optical images of a porous PAEK medical implant.
Figure 3A:
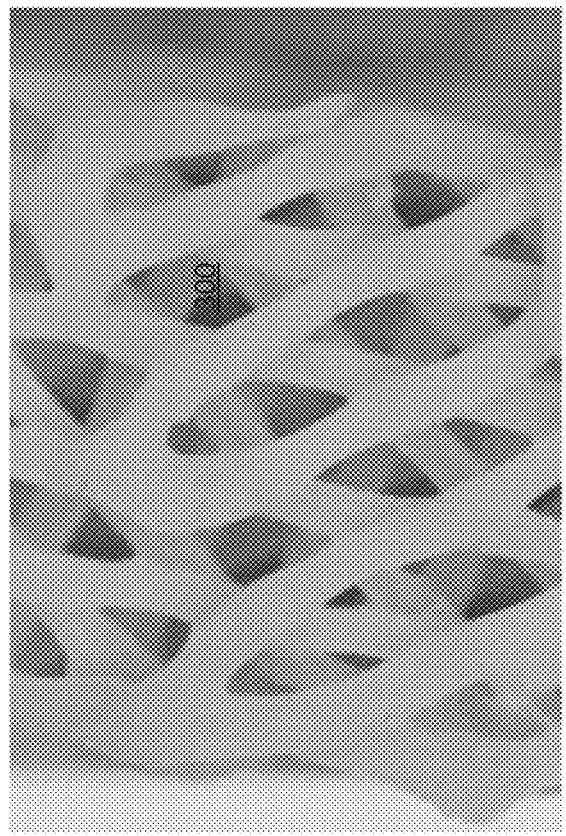
Figure 4B:
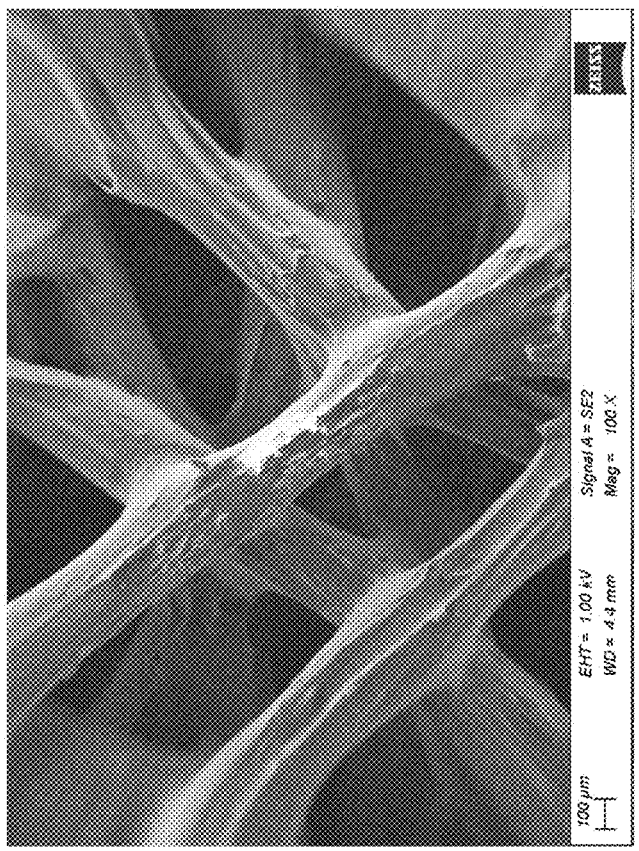
FIGS. 4A and 4B are scanning electron microscopy (SEM) images of a porous PAEK medical implant.
Figure 4A:
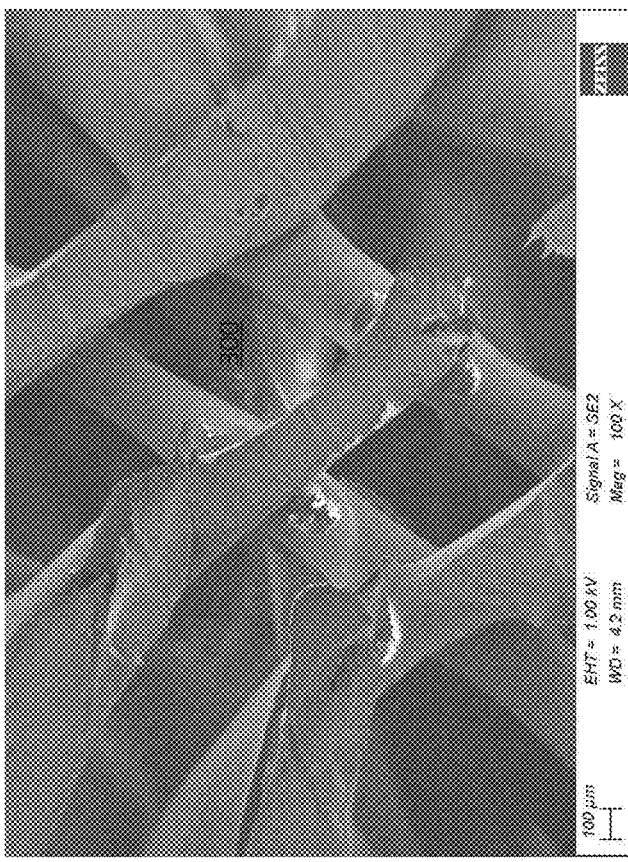

FIGS. 3A and 3B are photographs of porous PEEK medical implants, and FIGS. 4A and 4B are scanning electron micrographs of porous PEEK medical implant. These images illustrate the sparse, porous structure of the medical implant as well as the non-linear and non-uniform nature of the continuous length of PEEK between adjacent nodes. These images also illustrate the textured surface of the PEEK, discussed in more detail below.

As illustrated in FIGS. 3A-3B and 4A-4B, the continuous length or lengths of PAEK that make up the porous PAEK medical implant form a substantially periodic lattice structure defining a network of interconnected pores 300. A substantially periodic lattice structure is a structure composed of repeating units, with slight variations resulting from, e.g., manufacturing processes. In an example, the layers of PAEK form a triply periodic minimal surface (TPMS) lattice structure, e.g., a TPMS diamond lattice structure, a TPMS gyroid lattice structure, a TPMS rectilinear lattice structure, or a TPMS spherical lattice structure. In the example of FIGS. 3A-3B and 4A-4B, the layers of PAEK can form a TPMS diamond lattice structure that mimics the trabecular structure of bone, thus providing a strut anatomy that is similar to that provided by natural bone. A TPMS lattice structure has three-dimensional symmetry and a high ratio of surface area to volume. This structure has advantages in terms of biomechanics, e.g., providing advantageous system energetics and enabling stress dissipation and strain dispersion. A TPMS lattice structure also has advantages in terms of biology, e.g., facilitating fluid flow and permeability, mimicking cellular microenvironments (e.g., by providing appropriate oxygen levels), offering high surface area exposure, and promoting osseointegration.

Porous PAEK medical implants have a porosity of between 40% and 80% by volume, e.g., about 40%, about 50%, about 60%, about 70%, or about 80%. Interconnected pores are pores that are accessible from the exterior of the medical implant. The average dimension (e.g., diameter) of the pores 300 is between 50 μm and 1 mm, e.g., between 100 μm and 700 μm, between 100 μm and 500 μm, between 200 μm and 300 μm, or between 220 μm and 280 μm. In some cases, the pores are irregularly shaped, e.g., non-spherical. For instance, when the lattice structure of the medical implant is a TPMS diamond lattice structure, the pores are substantially diamond-shaped. The pore size and the porosity of the porous PAEK medical implants described here mimics the architecture of trabecular bone and provide a large amount of surface area for contact between bone and the medical implant, thereby facilitating osteogenesis.

The crystallinity of the PAEK in a porous PAEK medical implant differs between an interior portion and an exterior portion of the material. For instance, in at least some locations in a PAEK medical implant, the exterior surface of the continuous length of PAEK has a crystallinity that is greater than a crystallinity of the interior portion of the continuous length of PAEK. In a specific example, the interior portion of at least some of the continuous lengths of PAEK in a PAEK medical implant has a crystallinity that is less than 50% crystalline by volume, e.g., between 10% and 50%, between 20% and 40%, or between 25% and 35% crystalline by volume. The crystallinity of the interior portion is low enough that the interior portion appears translucent when imaged, e.g., exhibiting translucent brown bands. The exterior surface of these continuous lengths of PAEK includes crystalline domains, with amorphous regions interspersed therebetween. The crystallinity of the exterior surface is higher than that of the interior portion, e.g., between 10% and 50% by surface area. The crystallinity of the semi-crystalline exterior surface makes the surface appear opaque, e.g., with a light beige color. Without being bound by theory, it is believed that the processing conditions, e.g., the time and temperature profile of the fabrication process, enable formation of continuous lengths of PAEK having semi-amorphous interior portions and exterior surfaces with crystalline regions.

The crystalline domains on the exterior surface of the continuous length of PAEK have a lamellar surface microstructure. For instance, the crystalline domains 506 include plate-like, generally hexagonal crystals having a characteristic dimension (e.g., a thickness) of between 4 nm and 10 nm, e.g., between 6-10 nm, or about 5 nm, and in-plane dimensions (e.g., a length or diameter) of between 200 nm and 500 nm, e.g., 200 nm, 250 nm, 300 nm, 350 nm, 400 nm, 450 nm, or 500 nm. Multiple such lamellar crystals congregate together to form each crystalline domain. For instance, the crystalline domains can be spherules that have a radial microstructure and a dimension (e.g., diameter) or between 4 μm and 10 μm. e.g., between 4 μm and 8 μm or between 4 μm and 6 μm.

Figures 5A, 5B:
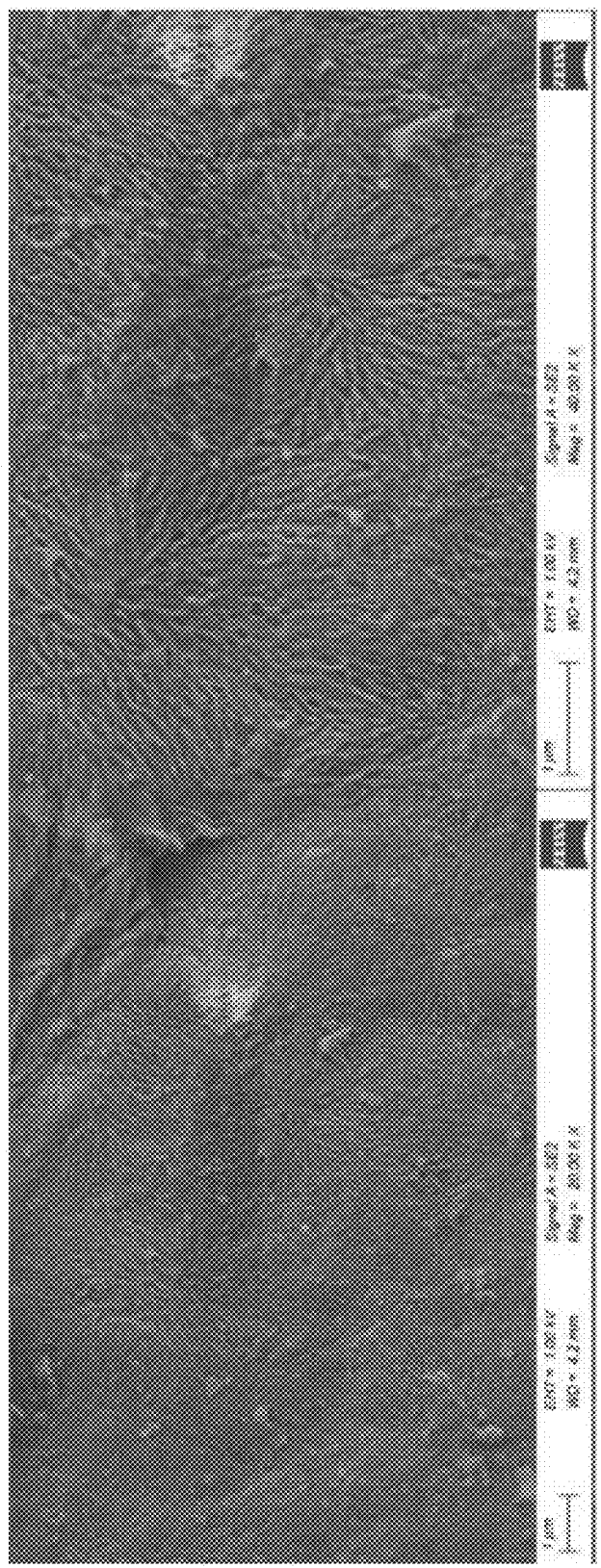
FIGS. 5A and 5B are SEM images of a porous PAEK medical implant.

FIGS. 5A and 5B are SEM images of a portion of a continuous length of PEEK of a medical implant, showing the radial microstructure of the spherules that form the crystalline domains, with the amorphous regions of the exterior surface separating the radial arms of the spherules.

The microstructure of the exterior surface of the continuous length of PAEK provides a surface roughness (e.g., root mean square (RMS) surface roughness) of between 0.5 μm and 3.0 μm, e.g., between 1 μm and 1.5 μm. Without being bound by theory, it is believed that this surface microstructure (e.g., the crystalline domains separated by amorphous regions, and the resulting surface roughness) mimics the surface microstructure of bone, thereby promoting osteogenesis.

In some examples, the relative crystallinity of the interior portion and exterior surface of the PAEK in a porous PAEK medical implant varies with location in the porous PAEK medical implant. The PAEK in layers that were formed early in the additive manufacturing process (e.g., layers at the bottom of the medical implant, as oriented in the additive manufacturing system, referred to as lower layer) can have a different amount and configuration of crystallinity than the PAEK in later layers (e.g., layers at the top of the medical implant, referred to as upper layers). The differences in crystallinity are visible optically, e.g., in optical microscopy images of thin cross-sections of a PAEK medical image (e.g., such as those obtained for histological imaging). In a transmitted light optical image, substantially amorphous regions of PAEK appear translucent while regions of higher crystallinity appear opaque. In some examples, there is a gradient of crystallinity within the opaque regions of higher crystallinity.

It is believed that the greater amount of thermal cycling experienced by the lower layers as compared to the upper layers contributes to this difference in microstructure. Lower layers of the medical implant are formed prior to upper layers, and as such, the lower layers experience more thermal cycling than the upper layers. This difference in the amount of thermal cycling experienced by layers at different locations in the medical implant contributes to differences in the microstructure of the PAEK.

The PAEK in the upper layers is deposited at a temperature close to the glass transition temperature of the PAEK. After deposition, the exterior surface of the PAEK cools quickly, solidifying an arrangement of unorganized polymer chains. The interior portion of the PAEK cools more slowly than the exterior surface, allowing a more organized, crystalline structure to develop in the interior portion. A similar cooling process occurs for the PAEK in the lower layers. However, the PAEK in these lower layers undergoes additional thermal cycling when overlying layers are deposited on top of existing, underlying layers. At the nodes where the overlying layer contacts the underlying layer, the freshly deposited layer remelts the exterior surface of the underlying layer. The material previously on the exterior surface at the node becomes an interior portion of the PAEK at the node, and cools more slowly, thus becoming more crystalline. Moreover, other exterior surfaces of the underlying layer of PAEK are also reheated by the deposition of the overlying layer, facilitating reorganization of the polymer chains on the exterior surface and enabling the crystallinity of the exterior surface to increase.

As a result of these differences in thermal cycling, the PAEK in the lower layers of a porous PAEK medical implant can have higher percentage crystallinity than the PAEK in the PAEK in the upper layers, e.g., there is a gradient in crystallinity from one side of the medical implant to another. Other orientations for the gradient in crystallinity can also be achieved, e.g., depending on the fabrication process. For instance, the porous PAEK medical implant can have a gradient in crystallinity that extends from the inner region of the implant to the outer region of the implant.

Moreover, each individual length of PAEK also has a gradient in crystallinity. Some lengths of PAEK, e.g., in later-deposited layers, have a gradient from a more crystalline interior portion of the PAEK to an exterior surface with lower crystallinity, e.g., because of the relatively rapid cooling of the exterior surface. Other lengths of PAEK, e.g., in earlier-deposited layers, have a gradient of increasing crystallinity from the interior portion to the exterior surface, e.g., because the re-melting of these layers provides time for the exterior surface to reorganize. In some examples, a post-deposition anneal can further increase the crystallinity of the exterior surfaces of the lengths of PAEK.

In some examples, exterior surfaces of continuous lengths of PAEK in a porous PAEK medical implant are coated with a coating, such as a hydroxyapatite (HA) coating, a tricalcium phosphate coating, or a calcium phosphate coating. The coating is a crystalline coating that extends throughout the porous structure of the medical implant, coating substantially all exterior surfaces of the PAEK. The coating is chemically bonded to the PAEK. As with uncoated PAEK, the exterior surface of at least some continuous lengths of coated PAEK in a porous PAEK medical implant has crystalline regions separated by amorphous domains, and has a higher crystallinity than the interior portion of the same continuous length of PAEK.

The coating is a thin coating, e.g., sufficiently thin such that bone can anchor directly to the exterior surfaces of the PAEK of the medical implant. Enabling bone to anchor directly to the PAEK, e.g., rather than to the coating itself, provides mechanical stability. For instance, the coating has a thickness of between 1 nm and 80 nm, e.g., between 1 nm and 50 nm, between 1 nm and 20 nm, or between 1 nm and 10 nm.

Figure 6B:
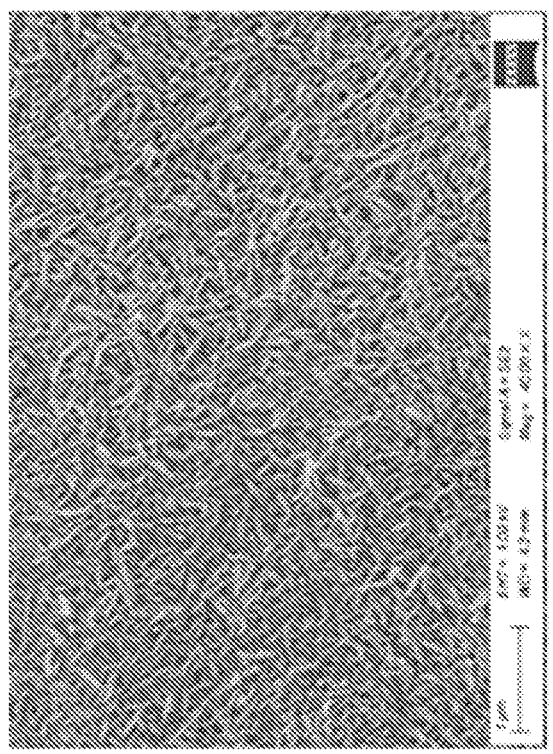
FIGS. 6A and 6B are SEM images of a porous PAEK medical implant.
Figure 6A:
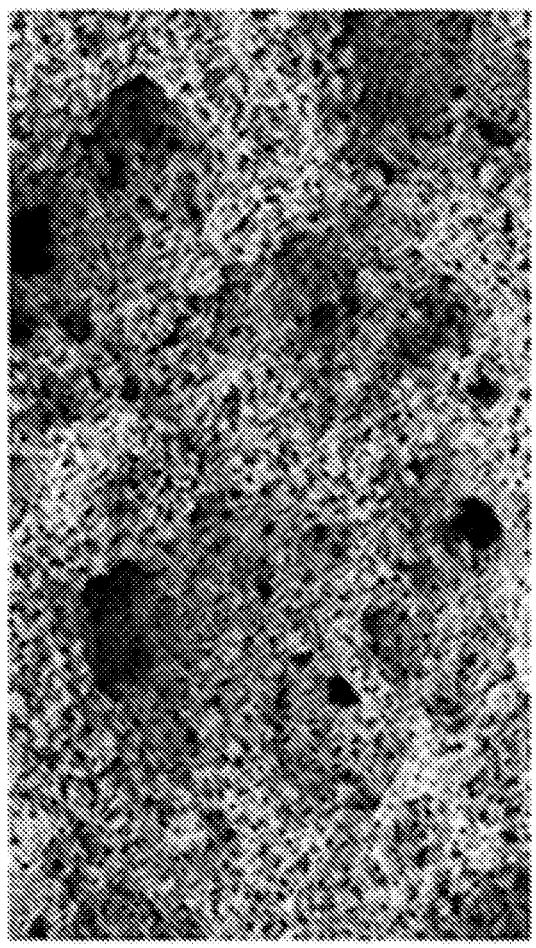

FIGS. 6A and 6B are SEM images of a PEEK medical implant with an HA coating. As shown in these images, the HA coating is a crystalline coating having elongated, needle-like crystals with a length of between 50 nm and 250 nm, e.g., between 50 nm and 100 nm.

Certain structural characteristics of the porous PAEK medical implant, including the network of interconnected pores, the pore size distribution, and the presence of bioactive components (e.g., the HA coating or other bioactive coating such as a tricalcium phosphate or calcium phosphate coating) contribute to the osteoconductive behavior of the porous PAEK medical implant. The bioactive components also contribute to the osteostimulatory behavior of the medical implant. Micro- and nano-structural characteristics, including surface crystallinity and surface roughness, contribute to the osteoinductive (e.g., immunomodulatory) behavior of the medical implant.

Figure 7:
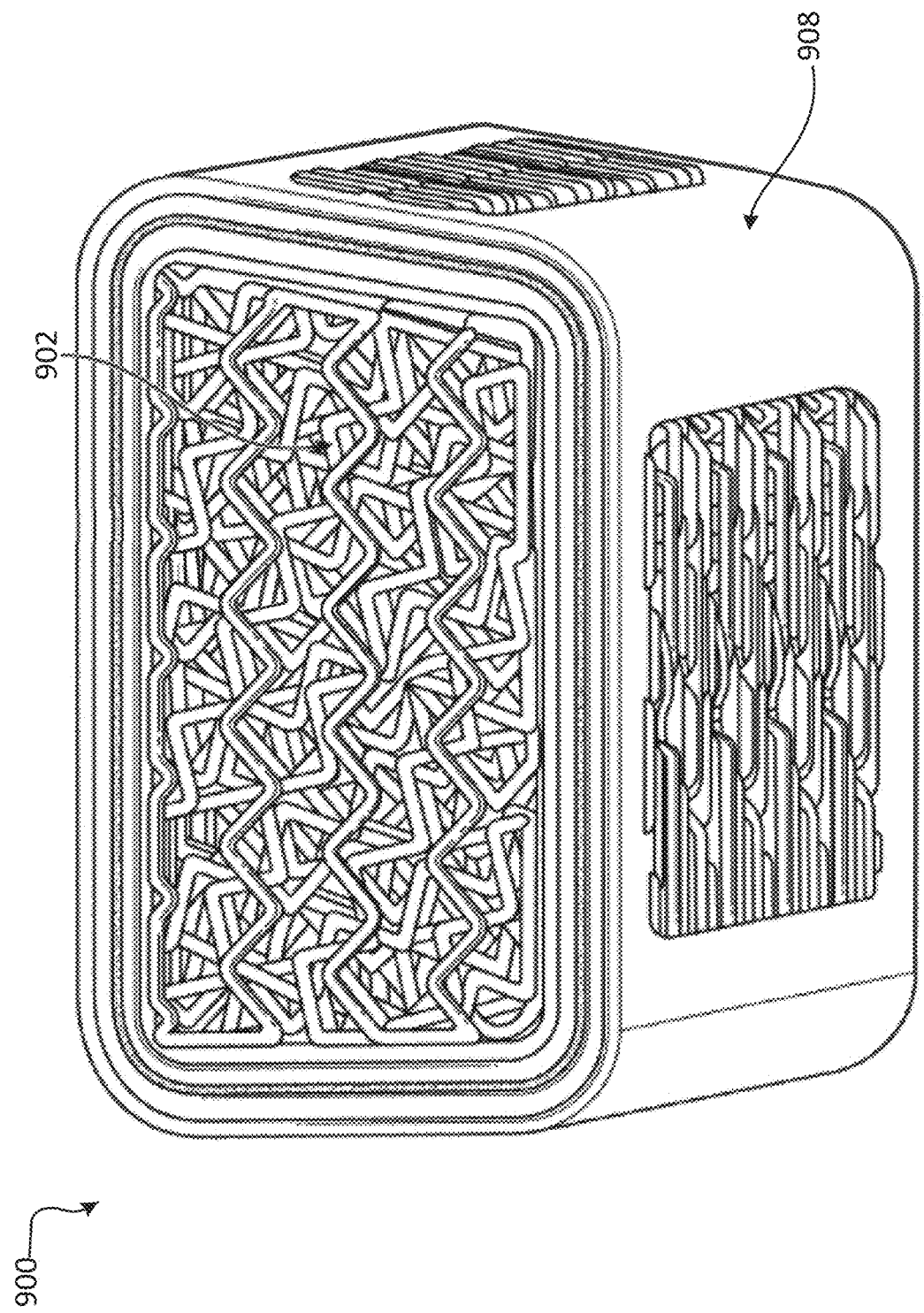
FIG. 7 is a diagram of a porous PAEK medical implant.
Figure 8A:
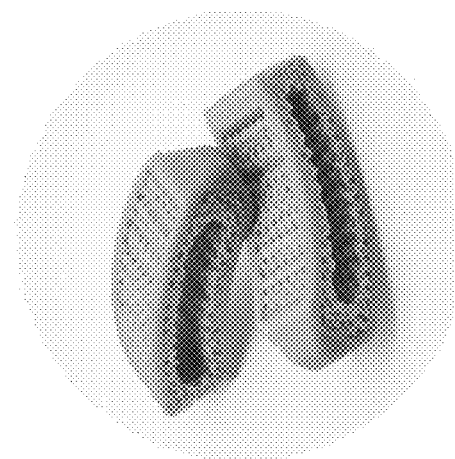
FIGS. 8A-8D are photographs of porous PAEK medical implants.
Figure 8B:
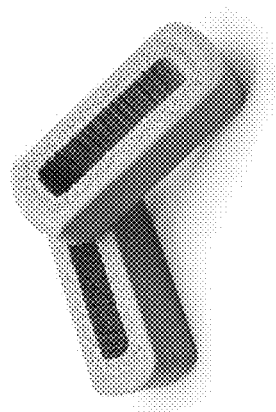
Figure 8C:
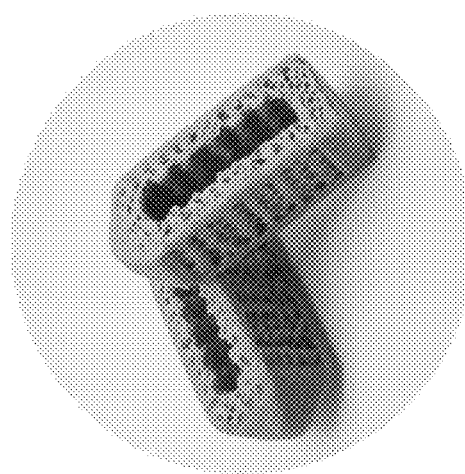
Figure 8D:
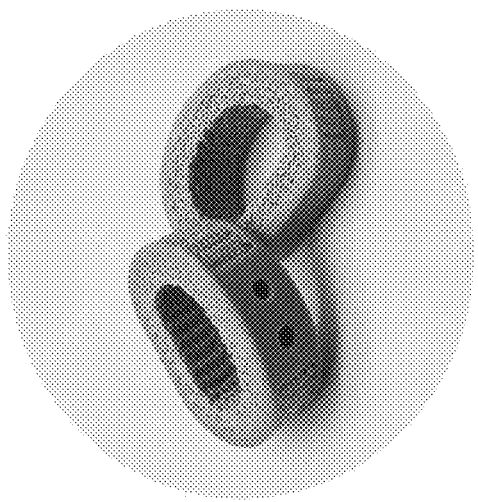

In some examples, a porous PAEK medical implant has multiple regions each having a different porosity. For instance, referring to FIG. 7, a porous PAEK medical implant 900 includes a first region 902 having a high porosity, e.g., a porosity of between 40% and 80%; and a second region 908 having a much lower porosity, e.g., a porosity of between 0% and 10%. In the example of FIG. 7, both regions 902, 908 span all of the layers of the porous PAEK medical implant (e.g., from a bottom surface to a top surface of the implant), but in some examples one or more of the multiple regions do not span all layers. In some examples, a continuous length of PAEK connects the two regions 902, 908 in at least one of the layers, e.g., meaning that extrusion of the length of PAEK is not interrupted even when printing of a region of different porosity begins.

Figure 9B:
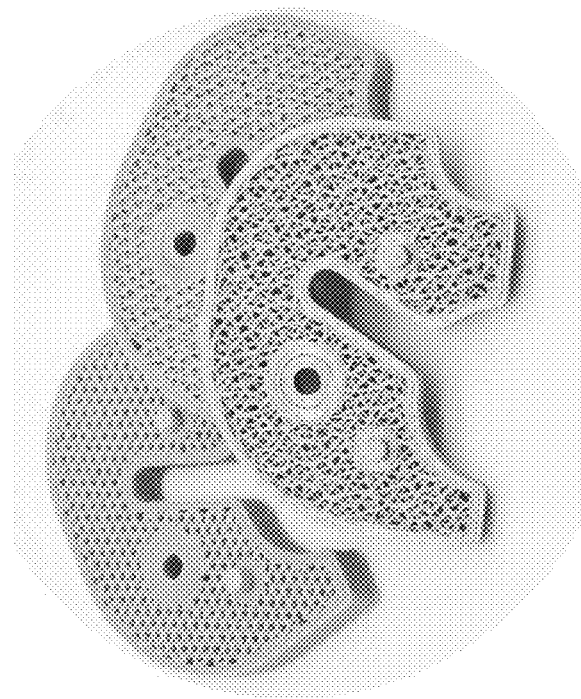
FIGS. 9A and 9B are photographs of porous PAEK medical implants.
Figure 9A:
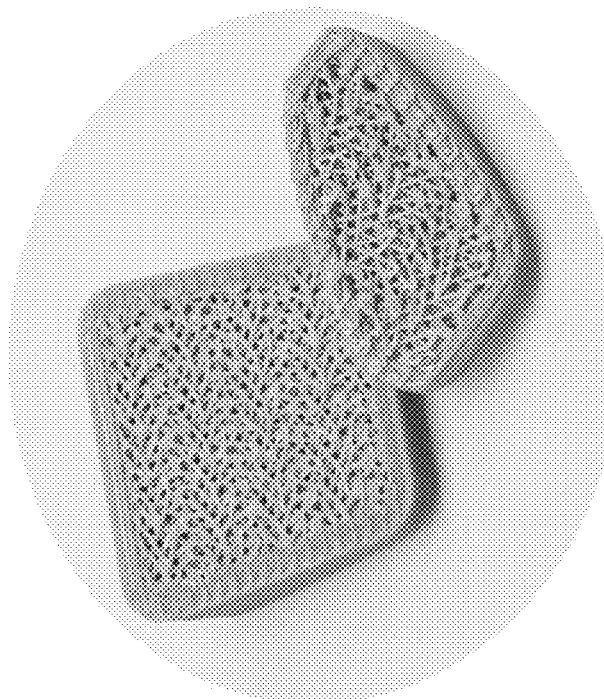

The porous PAEK medical implants described here can be structured for use in various anatomical contexts. The porous PAEK medical implant of FIG. 1 is a cervical implant. Referring to FIGS. 8A-8D, other types of spinal implants can be porous PAEK medical implants, including posterior lumbar interbody fusion implants (PLIF, see FIG. 8A), transforaminal lumbar interbody fusion implants (TLIF, see FIG. 8B), anterior lumbar interbody fusion implants (ALIF, see FIG. 8C), direct lateral interbody fusion implants (DLIF, see FIG. 8D), or extreme lateral interbody fusion implants (XLIF). Referring to FIGS. 9A and 9B, porous PAEK medical implants can be implants for extremities (FIG. 9A), such as tibial plateau implants, cotton implants, or Evans wedge implants, or implants for large joints (FIG. 9B). The medical implants described here can also be cranial implants or maxillofacial implants, or can be used for reconstruction of bones, e.g., interior bones, foot or ankle bones, hand or wrist bones, or other suitable bones.

Porous PAEK structures can be used in other medical applications, such as for drug delivery or for neurological applications. Porous PAEK structures can also be structured for use in non-medical contexts. For instance, porous PAEK structures can be used in aerospace applications, e.g., for aircraft engine parts (e.g., due to its high heat resistance and performance at high temperature), aircraft exterior parts (e.g., due to its rain erosion resistance), or other aerospace applications (e.g., as a replacement for aluminum due to its light weight); in automotive applications, or in other suitable contexts.

Although we refer to porous PAEK structures here, these porous, additively manufactured structures can also be formed of other materials, including polycaprolactone (PCL), poly(L-lactide) (PLLA), poly(glycolic acid) (PGA), polysulfone (PSF), or other polymers. In some examples, these porous, additively manufactured structures can be composites, e.g., polymer composites, e.g., layered polymer composites. They can contain ceramics or slurries, biologics, cellular material, or proteins.

The porous PAEK structures (e.g., medical implants) described here have mechanical properties that are suitable for the context in which the structures are to be used. For instance, porous PAEK medical implants have mechanical properties that are comparable to those of physiologic bone of the target implant site. Unless stated otherwise, the mechanical characteristics described here were measured according to ASTM F2077 test standards.

The Young's modulus of elasticity of the porous PAEK structures described here is between 0.3 GPa and 4.0 GPa, e.g., 0.3 GPa and 3.0 GPa, between 0.8 GPa and 1.5 GPa, or between 1.0 GPa and 1.2 GPa. A Young's modulus in this range is comparable to the Young's modulus of cancellous bone.

The compression strength of the porous PAEK structures is at least 20 kN, e.g., between 20 kN and 150 kN, between 20 kN and 100 kN, between 20 kN and 40 kN, or between 22 kN and 30 kN. A compression strength in this range is significantly higher than the compression strength of physiologic bone (e.g., compressed cancellous bone), e.g., at least twice or at least six times as high, e.g., between 2-10 times as high.

The fatigue strength of the porous PAEK structures described here is between 1200 N and 1800 N, e.g., 1500 N, at 5 million cycles of 5 Hz. The stiffness of the porous PAEK structures described here is between 0.8 GPa and 1.5 GPa, e.g., between 1.0 GPa and 1.2 GPa.

Other mechanical properties of the porous PAEK structures, such as torsion, compression-shear, and subsidence, are also comparable to those of physiologic bone of the target implant site.

Without being bound by theory, it is believed that the crystalline microstructure of the porous PAEK structures described here, in which a semi-amorphous interior portion is enclosed in a crystalline exterior surface, contributes to these mechanical properties. For instance, the crystallization of the exterior surface, which occurs upon cooling of the PAEK after printing (as discussed further below), creates a surface compression layer which lends strength and stiffness to the lengths of PAEK and thus to the structure as a whole. Moreover, the porous lattice structure, e.g., the TPMS diamond structure with interconnected porosity, also contributes to the strength, modulus, and toughness of the structure.

Figure 10:
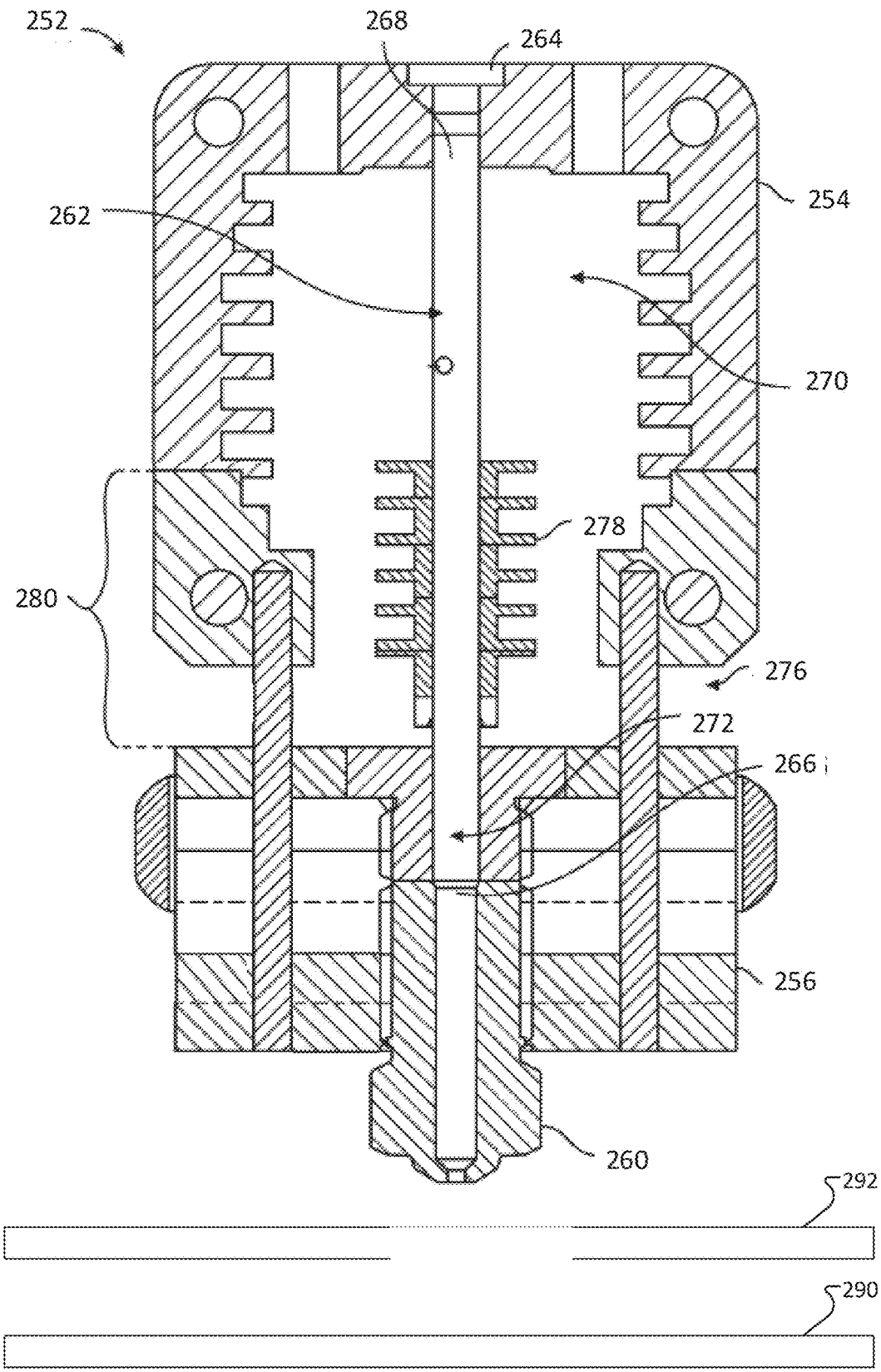
FIG. 10 is a diagram of an components of an additive manufacturing system.

Referring to FIG. 10, the porous PAEK medical implants described here are produced using an additive manufacturing system that implements an additive manufacturing process such as fused strand deposition, fused filament fabrication, or fused melt deposition. As noted above, the time and temperature profile of the additive manufacturing process contribute to the non-linear and non-uniform nature of the continuous lengths of PAEK that make up the medical implants, and to the surface microstructure of the PAEK.

The system includes a print head 252 for heating and dispensing printing material, such as a PAEK filament, from a nozzle 260 of the print head 252 onto a build plate 290. The filament is fed into a feed tube 262 of the print head 252 via an inlet 264, which is connected via an internal passage 268 to an outlet 266 of the feed tube. The internal passage 268 of the feed tube 262 has an upstream portion 270 and a downstream portion 272. As the PAEK filament passes through the downstream portion 272 of the feed tube 262, a heater 256 heats the filament to a temperature that is significantly above the melting point of the PAEK, e.g., between 50-100° C. above the melting point. For instance, the heater 256 heats the filament to a temperature of between 325° C. and 475° C. In a specific example, when the filament is PEEK, which has a melting temperature of around 340° C., the heater 256 heats the filament to a temperature of between 400° C. and 500° C., e.g., between 400° C. and 450° C., e.g., 430° C. As discussed further below, heating the PAEK to a temperature significantly above its melting point enables the extruded PAEK to stay in the molten state immediately upon deposition, which contributes to the non-linear and non-uniform porous structure discussed above.

The upstream portion 270 of the feed tube 262 is cooled by a cooler 254 to regulate the temperature of the PAEK filament as it passes through the feed tube 262. The cooler 254 is spaced upstream from the heater 256, with a gap 276 separating the cooler 254 from the heater 256. In some examples, a secondary cooler 278 directly cools the PAEK filament in the feed tube 262.

A hot zone 280 separates the heat generated by the heater 256 from the cooler temperatures in the region of the cooler 254 and secondary cooler 278. The presence of the hot zone 280 enables the PAEK filament to remain in a solid state until it reaches the hot zone 280, at which point it begins to transition from a solid to a molten state. This configuration prevents heat from the heater 256 from melting PAEK filament in the upstream portion 270 of the feed tube, which could cause premature crystallization of the PAEK.

The molten filament of PAEK is extruded through the nozzle 260 and onto the build plate 290 to form the porous PAEK structure. The build plate 290 is rotated relative to the nozzle 260 between formation of each successive layer of PAEK, e.g., rotated by between 20° and 60°, e.g., between 20° and 40° or between 30° and 40°, e.g., about 36°. This rotation, together with the sparse fill of each layer, means that much of the PAEK in an overlying layer is unsupported by the underlying layer. This unsupported, porous structure, together with the temperature profile during extrusion, contributes to the microstructure of the resulting porous PAEK structure.

The rate at which the PAEK filament is extruded from the nozzle 260 and the rate at which the nozzle 260 moves relative to the build plate 290 during extrusion (referred to as the feed rate) also impacts the microstructure of the resulting porous PAEK structure. For instance, for a nozzle diameter of between 0.2 mm and 0.5 mm, the extrusion rate of PAEK can be between 2 mm/s and 20 mm/s, e.g., between 10 mm/s and 15 mm/s. The feed rate can be between 5 mm/s and 20 mm/s, e.g., between 8 mm/s and 12 mm/s or between 10 mm/s and 20 mm/s. A faster extrusion rate and a faster feed rate both result in deposition of a thinner bead of PAEK.

The ratio between the extrusion rate and the feed rate is referred to as the extrusion ratio. In general, filaments of PAEK are extruded at an extrusion ratio of between 0.5 and 4.0, e.g., between 0.5 and 2.0 or between 0.6 and 1.0. A smaller extrusion ratio (e.g., a lower extrusion rate for the same feed rate) results in deposition of a thinner bead, which can exhibit attenuation (e.g., non-linearity and non-uniform diameter) in the unsupported portions of the deposited PAEK.

Local variations in the microstructure of the porous PAEK structure can occur, e.g., due to the extrusion path. For instance, as the extrusion path rounds a corner from one row to another, the extruded PAEK experiences an acceleration and deceleration that result in bulges on the upstream side of the corner and attenuation on the downstream side of the corner. These microstructural variations provide micron-scale roughness to the resulting porous PAEK structure, e.g., mimicking the microstructure of physiologic bone.

The print plane, and the in-progress PAEK structure thereon, is maintained at a temperature of around the glass transition temperature of the PAEK, e.g., at a temperature of between 130° C. and 160° C. In some examples, the temperature of the print plane is maintained by a reflector plate 292, which can be constructed of a material having passive heat reflecting properties or which can include an active heating element, or both. In some examples, the temperature of the print plane is maintained by a heating layer disposed under the build plate 290 (e.g., on the opposite side of the build plate 290 from the print head 252). In some examples, both a reflector plate and a heating layer are used. The operation of the reflector plate 292, the heating layer, or both can be controlled via closed loop feedback control to maintain the print plane at the target temperature.

Maintaining the print plane at a temperature of around the glass transition temperature of the PAEK keeps the printed PAEK in its glassy state. This in turn enables bonding between the lengths of PAEK of adjacent layers. For instance, when a strand of molten PAEK is extruded from the nozzle 260 of the print head 252, the molten PAEK re-melts the PAEK of the underlying, already-printed layer, enabling the two lengths of PAEK to bond and form a node. This re-melting and bonding is facilitated further by the extrusion of the PAEK at temperatures significantly above the melting point of the PAEK; the hot extruded PAEK stays above its melting point following extrusion from the nozzle 810 for long enough to re-melt and bond to the PAEK of the underlying layer.

Extruding PAEK at a temperature significantly above its melting point, and maintaining the print plane at a temperature of around the glass transition temperature of PAEK, also enables formation of the non-linear and non-uniform lengths of PAEK between nodes of the structure. After the extruded PAEK bonds to the PAEK of the underlying layer, forming a node, the molten PAEK is stretched across an unsupported space before reaching another PAEK support and forming another node. This attenuation of the PAEK between nodes causes non-uniformity in its diameter: the PAEK is stretched to a thinner diameter between the nodes and remains at a larger diameter at the nodes. The stretching of the PAEK also results in drooping of the unsupported, molten or glassy PAEK into the plane of the underlying layer. It is believed that the stretching of the PAEK also causes twisting of the unsupported lengths of PAEK, which further contributes to the surface microstructure of the PAEK.

Maintaining the print plane at a temperature around the glass transition temperature of the PAEK also contributes to the resulting crystalline structure of the PAEK, which has a semi-amorphous interior portion and an exterior surface having a crystalline (e.g., lamellar) microstructure. For instance, the slow cooling facilitated by the long residence at the glass transition temperature enables crystallization of the exterior surface. Moreover, the re-melting of previously extruded PAEK at the nodes when the next layer of PAEK is deposited further lengthens the cooling time and contributes to the surface crystallization.

Following the additive manufacturing process, the porous PAEK medical implant is annealed. The anneal is carried out at a temperature that is less than the glass transition temperature of the PAEK. For instance, when the medical implant is made of PEEK, which has a glass transition temperature of around 140° C., the porous PEEK medical implant is annealed at a temperature of between 150° C. and 300° C., e.g., between 150° C. and 200° C., for a period of between 1 hour and 10 hours. After manufacturing, the exterior surface of the PAEK in the medical implant the lamellar surface microstructure described above with respect to FIGS. 6A-6B.

In some examples, a coating, such as a hydroxyapatite coating, is disposed on the surface of the porous PAEK medical implant following the additive manufacturing process and following the anneal. The coating can be disposed by coating processes such as dip coating, immersion coating, or spray coating. The coating is disposed on all surfaces of the porous PAEK medical implant, e.g., extending through the internal porous structure of the medical implant.

EXAMPLES

All testing performed on PEEK articles formed by fused filament fabrication with the following parameters unless otherwise noted.

Example 1: Mechanical Properties

Mechanical properties, including compression strength, elastic modulus, and fatigue strength of PEEK cervical implants fabricated as described above were tested. Unless stated otherwise, the mechanical characteristics described here were measured according to ASTM F2077 test standards.

Figure 11B:
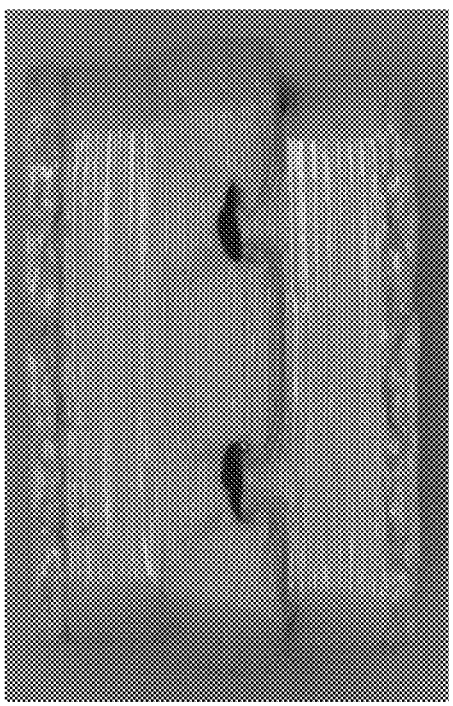
FIGS. 11A-11C are results of compression tests.
Figure 11C:
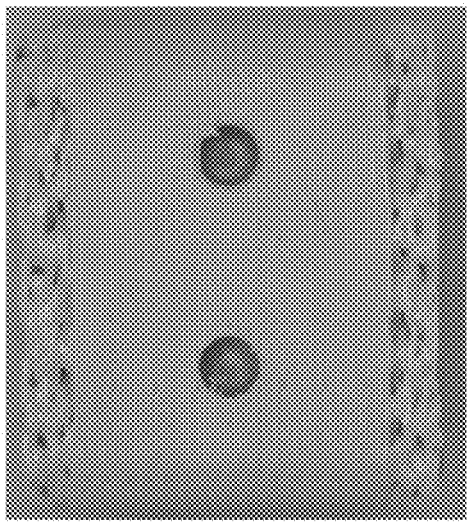
Figure 11A:
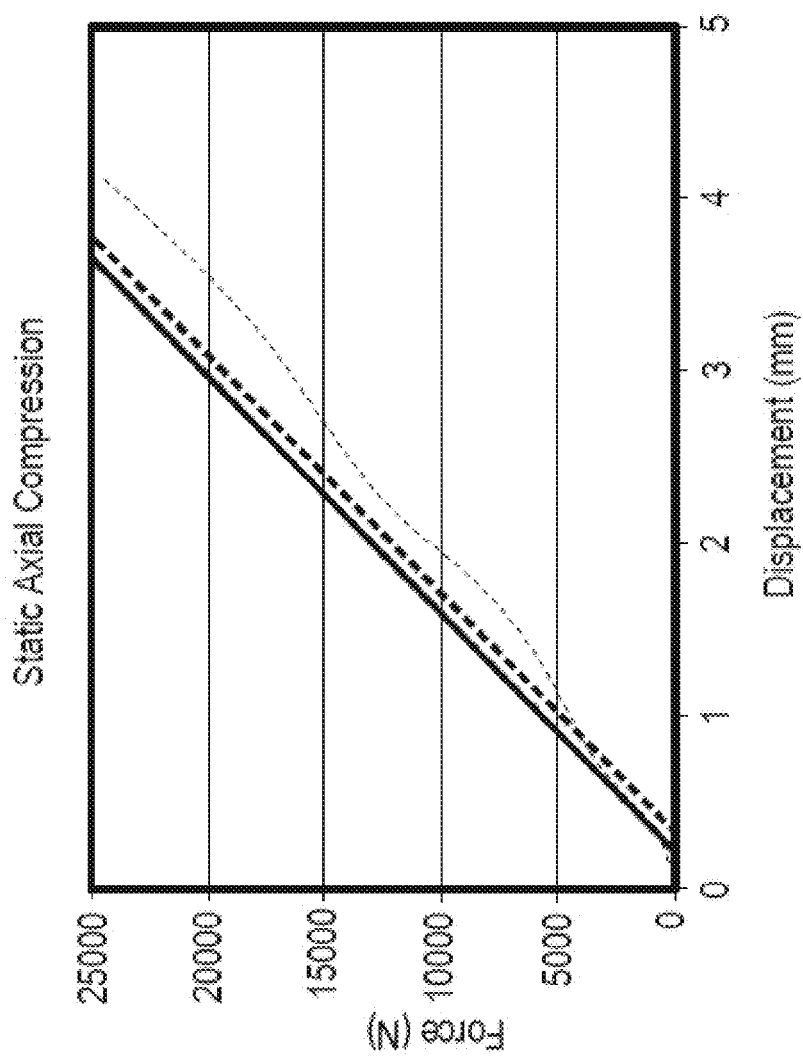

Referring to FIGS. 11A and 11B, the compression strength of the PEEK cervical implant was measured using a static axial compression test. Referring specifically to FIG. 11A, the compression strength of the PEEK cervical implant was found to exceed 25 kN, meaning that the PEEK cervical implant partially failed upon application of a 25 kN force. FIG. 11B is a photograph of the PEEK cervical implant after application of 25 kN of compressive force, and shows that the implant remains substantially intact and has only partially failed.

The modulus of elasticity of the PEEK cervical implant was measured to be 1.0 GPa, which is comparable to the elastic modulus of cancellous bone.

The fatigue strength of the PEEK cervical implant was measured using a dynamic axial compression test that was performed according to ASTM F2077. The PEEK cervical implant withstood application of 5 million cycles of 1500 N of force applied at 5 Hz and remained structurally intact. FIG. 11C is a photograph of a PEEK cervical implant after completion of the dynamic axial compression test.

Stiffness of the PEEK cervical implant was established during static axial compression testing. The PEEK cervical implant was tested at Kd=13,623 N/mm, which is approximately the $75^{th}$ percentile of FDA published data.

Further mechanical testing was performed on porous PEEK cervical interbody cages without radiographic markers to confirm that the PEEK structure, and not the radiographic markers, gives rise to the observed mechanical properties.

Figure 12A:
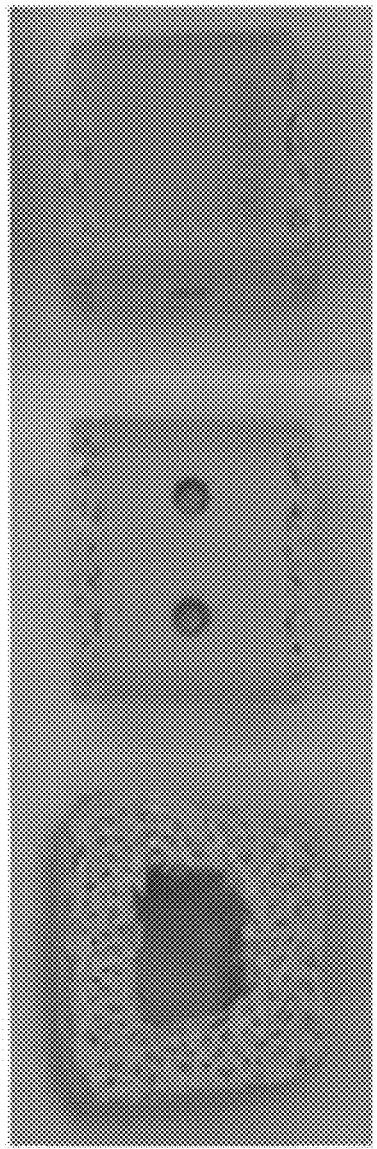
FIGS. 12A-12B are results of mechanical tests.
Figure 12B:
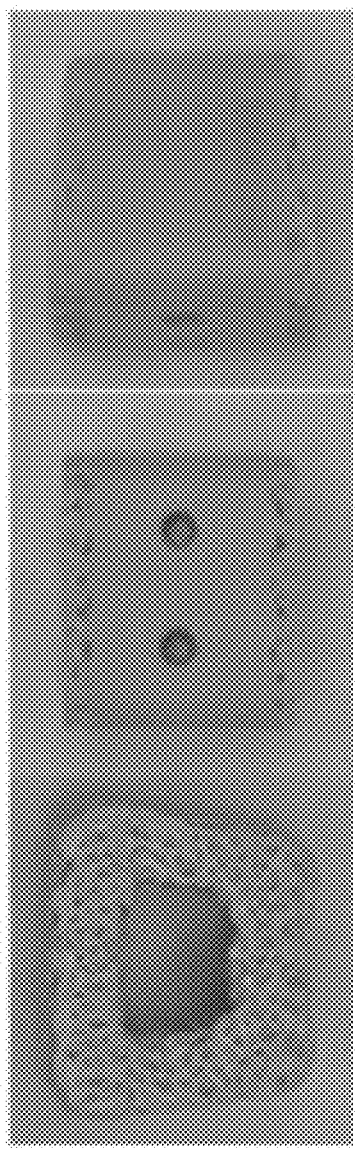

PEEK cervical interbody implants without radiographic markers were subjected to dynamic axial compression testing. FIG. 12A shows photographs of an implant prior to the testing, and FIG. 12B shows photographs of the implant after 5,00,000 cycles. As shown in the photographs, substantially no mechanical damage was caused by the dynamic axial compression testing. Height measurements for each of two specimens are shown in Table 1, confirming that the implants remained structurally intact:

TABLE 1

Dynamic axial compression testing height measurements of PEEK implants without radiographic markers, after 5,000,000 cycles

| | Overall Height Loss | | | Dense Region Height Loss | | |
|---|---|---|---|---|---|---|
| Sample | Delta from Pre-Test: Anterior (mm) | Delta from Pre-Test: Mid-Line (mm) | Delta from Pre-Test: Posterior (mm) | Delta from Pre-Test: Anterior (mm) | Delta from Pre-Test: Mid-Line (mm) | Delta from Pre-Test: Posterior (mm) |
| 1 | −0.16 | −0.03 | −0.07 | −0.08 | −0.08 | −0.03 |
| 2 | −0.37 | −0.48 | −0.38 | −0.03 | −0.04 | −0.05 |

PEEK cervical interbody implants without radiographic markers were also subjected to drop weight clinical impact testing. Samples were tested according to the test parameters listed in Table 2.

TABLE 2

Drop weight clinical impact testing parameters

| Sample | Impact Energy (J) | Velocity (m/s) | Drop Height (m) | Number of Impacts |
|---|---|---|---|---|
| 1 | 1.54 | 1.41 | 0.10 | 4 |
| 2 | 3.08 | 1.99 | 0.20 | 2 |
| 3 | 4.62 | 2.43 | 0.30 | 1 |
| 4 | 6.16 | 2.81 | 0.40 | 1 |

Drop weight testing results, shown in Table 3, demonstrate that the implants remained structurally intact:

TABLE 3

Drop weight clinical impact testing results

| | Overall Height Loss | | | Dense Region Height Loss | | |
|---|---|---|---|---|---|---|
| Sample | Delta from Pre-Test: Anterior (mm) | Delta from Pre-Test: Mid-Line (mm) | Delta from Pre-Test: Posterior (mm) | Delta from Pre-Test: Anterior (mm) | Delta from Pre-Test: Mid-Line (mm) | Delta from Pre-Test: Posterior (mm) |
| 1 | −0.03 | −0.05 | −0.01 | −0.02 | 0.00 | −0.05 |
| 2 | −0.04 | −0.03 | 0.00 | 0.00 | −0.02 | 0.00 |
| 3 | −0.06 | −0.13 | −0.02 | 0.00 | −0.03 | 0.00 |
| 4 | −0.01 | −0.14 | −0.07 | −0.03 | −0.04 | 0.07 |

Example 2: Biological Activity of Porous PEEK Structures

The osteogenic potential of PEEK cervical implants having various microstructures and surface chemistries were characterized with respect to human bone marrow stromal cell (hBMSC) osteogenesis. This assay determines whether hBMSCs, after exposure to specific surfaces, transition into osteoblasts, which are bone forming cells. This transition is primarily demonstrated by surface cell markers and the resulting gene expression and protein production. Materials demonstrating this cellular transition are said to possess osteogenic potential. As shown in this example, porous PEEK cervical implants were shown in this assay to possess osteogenic potential.

Figure 13:
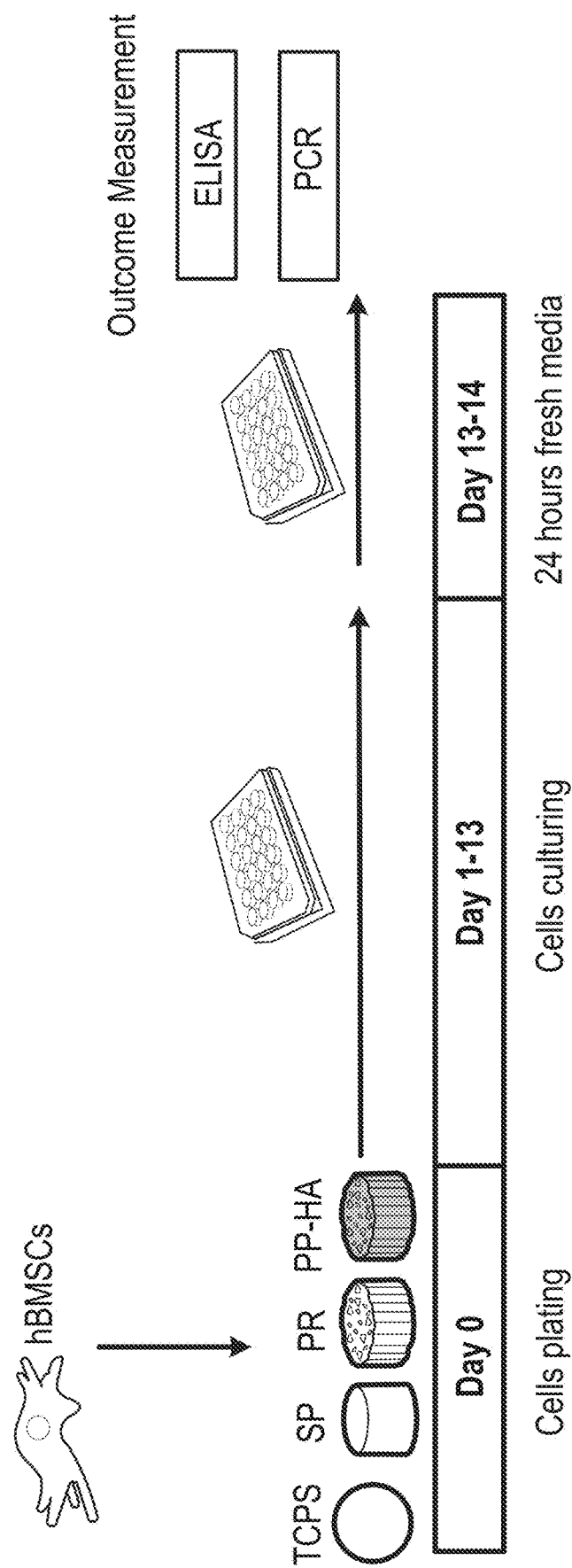
FIG. 13 is a test process flow.

FIG. 13 illustrates a test process flow. At day zero of the test, hBMSCs were plated onto four substrates: tissue culture polystyrene (TCPS) as a control, a porous PEEK cervical implant fabricated as described above (PP), a porous PEEK cervical implant having an HA coating (PP-HA), and a solid PEEK block (SP). The cells were cultured for fourteen days, after which the cultures were exposed to 24 hours of fresh, conditioned media. Cell layer lysates were extracted and measured for outcomes including osteocalcin, osteopontin, osteoprotegerin, vascular endothelial growth factor (VEGF), and DNA. Measurements of interleukins including IL-4, IL-10, and IL6, BMP-2, BMP-4, BgLAP, RUNX-2, and SP7 were also conducted.

Figure 14:
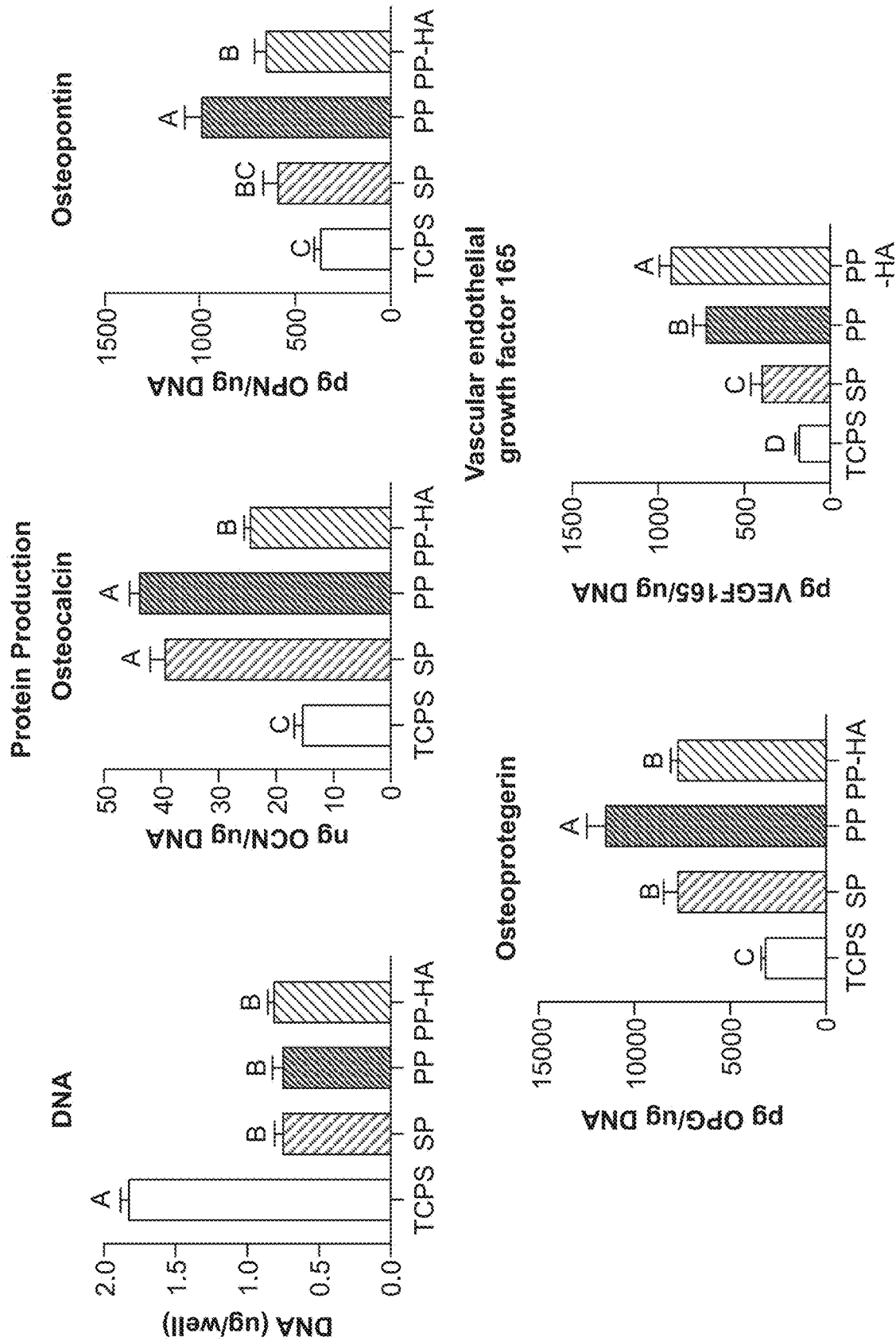
FIG. 14-16 are plots of results of human bone marrow stromal cells (hBMSC) assays.
Figure 15:
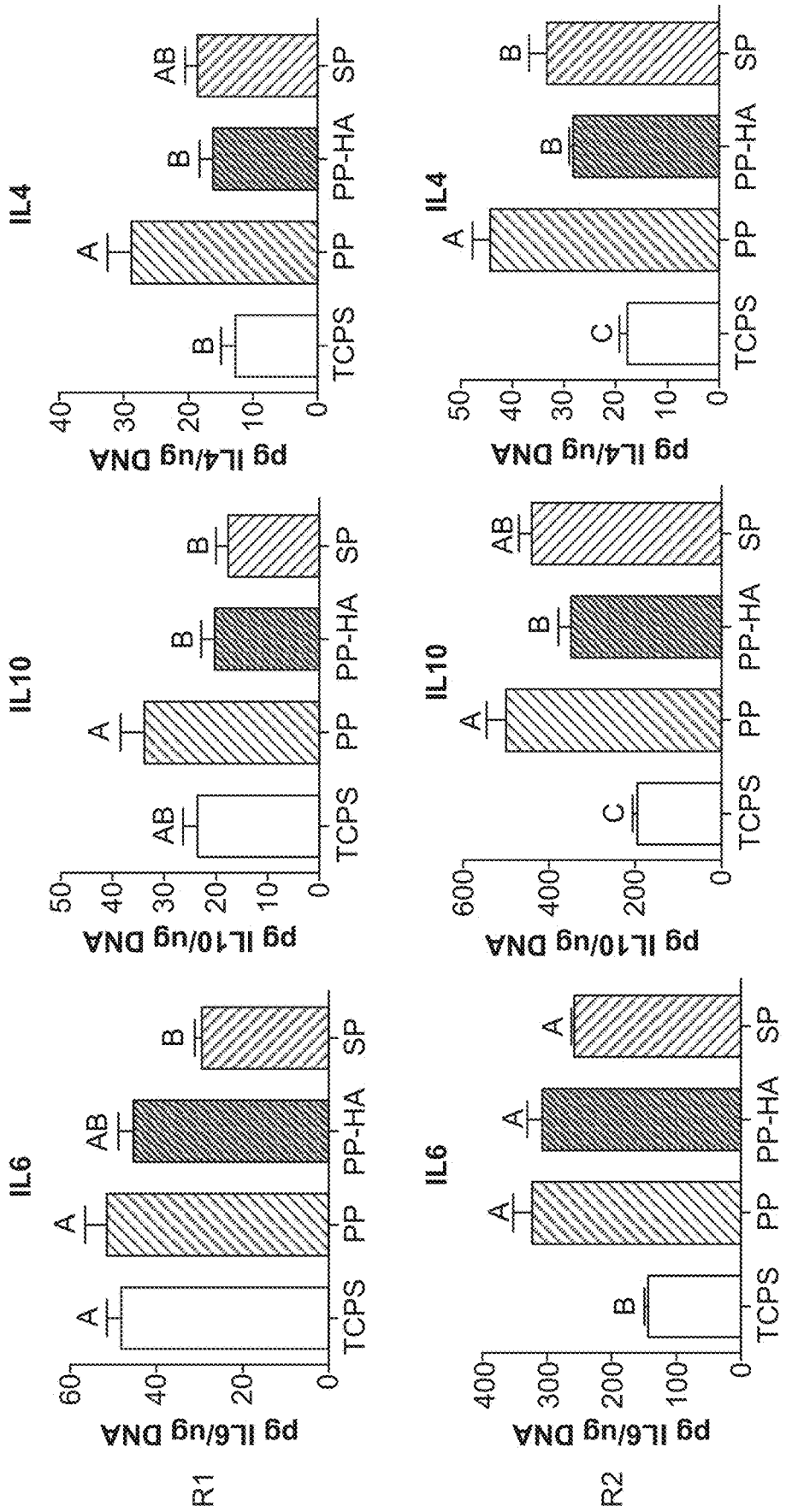
Figure 16:
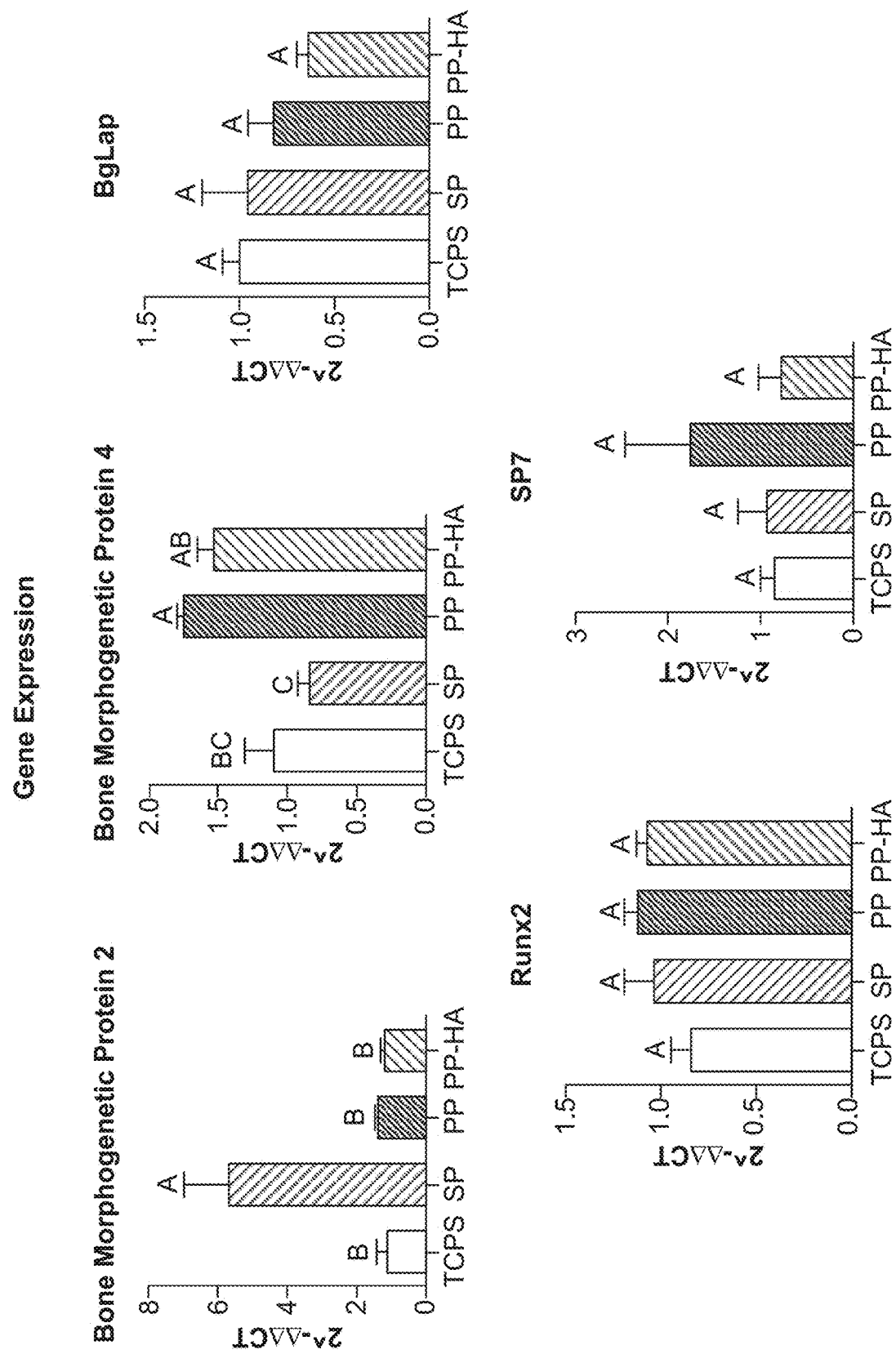

FIG. 14 show results of the hBMSC assays demonstrating the effect of the various surface chemistries and microstructures on the osteogenic potential of the structure, as indicated by protein production, including the concentration of DNA, osteocalcin, osteopontin, osteoprotegerin, and vascular endothelial growth factor 165. FIG. 15 shows interleukin production, again demonstrating the effect of surface chemistry and microstructure on the osteogenic potential of the structure. The top and bottom rows of FIG. 15 represent two different experimental runs, showing generally consistent results. Referring to FIG. 16, the hBMSC cultures described above were also assayed to characterize gene expression for further indication of osteogenic potential of the structures.

A summary of the results and their significance is provided in Table 4.

TABLE 4

Osteogenic potential assay results.

| | | +up/−down regulation | |
|---|---|---|---|
| Genes/Proteins | Function | PP | PP − HA |
| OCN (Osteocalcin) | Mineralization protein | + | − |
| OPN (Osteopontin) | Regulates Osteoclast upregulation | + | +/− (no diff) |
| OPG (Osteoprotegrin) | Regulates Osteoclast upregulation | + | +/− |
| VEGF (Vascular Endothelial Growth Factor) | Angiogenesis | + | ++ |
| IL-4, IL-10 Interluekins | | + | + |
| IL-6 Interluekins | Inflammation | − | − |
| BMP-2, −4, BgLAP, RUNX-2, SP7 | Osteogenesis upregulation | + | + |

Osteocalcin is a mineralization protein. The presence of osteocalcin indicates the presence of osteoblasts, thus indicating the existence of an environment conducive to bone generation. These results show upregulation of osteocalcin: the cultures from all three PEEK samples have higher osteocalcin concentrations than the TCPS culture. Osteopontin and osteoprotegerin are proteins that promote bone formation, and specifically that regulate osteoclast upregulation. As shown in these plots, while the cultures from all three PEEK samples have higher osteopontin and osteoprotegerin concentrations than the TCPS culture, the porous PEEK (PP) culture exhibits a significantly higher concentration of each protein than the other PEEK samples. Vascular endothelial growth factor (VEGF) contributes to angiogenesis. The concentration of VEGF in the cultures from all three PEEK samples is higher than in the TCPS culture, with the two porous PEEK cultures (PP and PP-HA) having the highest concentrations. These results are positive indicators of the osteogenic potential of porous PEEK.

The gene expression results are also positive indicators of the osteogenic potential of porous PEEK. The final group (BMP-2. -4, BgLAP, Runx2, SP7) were all either upregulated or showed no change.

In total, the upregulation of OCN, OPN, OPG, VEGF, IL-4, and IL-10 concurrent with the downregulation of IL-6 relative to solid PEEK indicated that both porous PEEK (PP) and porous PEEK having an HA coating (PP-HA) demonstrate osteogenic potential. While different proteins may express at different time periods during physiologic bone formation, the results of this cellular (in vitro) assay are consistent with the behavior of known bone forming (osteogenic) materials.

Figure 17:
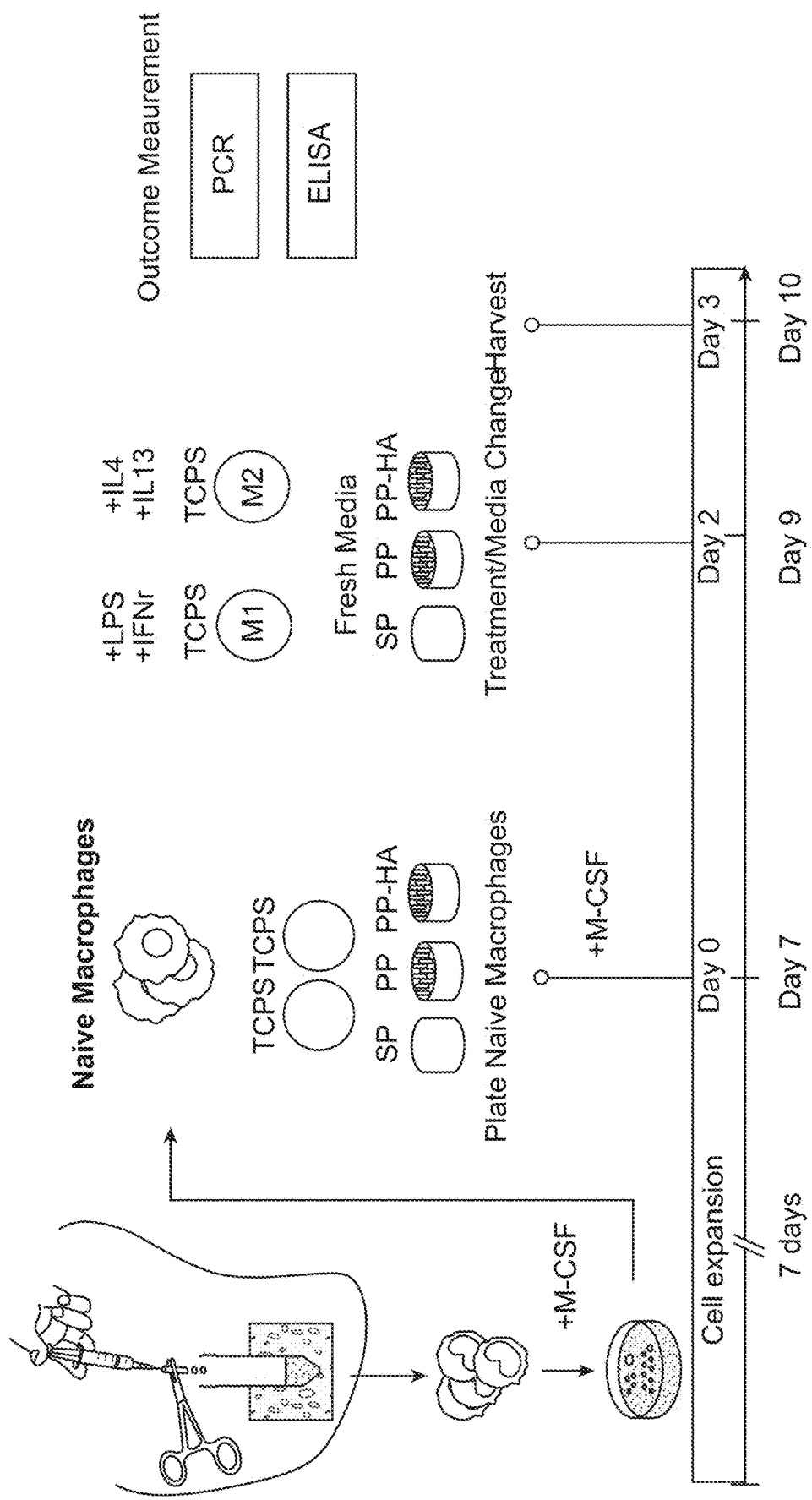
FIG. 17 is a test process flow.

Referring to FIG. 17, in another experiment, a macrophage polarization assay was performed to characterize the immunomodulatory potential of the implants. A macrophage polarization assay validates for naïve macrophages (e.g., present at early onset of inflammation, injury, or surgery) responding to specific surfaces. M1 macrophages remove debris and elicit pro-inflammatory cytokines, while macrophages transitioning to an M2 phenotype are pro-regenerative macrophages. The M1 phenotype macrophages exhibit specific gene expression that leads to fibrous tissue formation. The M2 phenotype macrophages release different proteins that lead to pro-regenerative, anti-inflammatory regeneration leading to bone formation.

The indicators of pro-inflammatory M1 macrophages result in iNOS, TNF-α, IL-6 and IL-1β expression. The indicators of pro-regenerative (anti-inflammatory) M2 macrophages result in Arg1, Mrc1, TGF-β1, IL-4, and VEGF expression. As demonstrated below, consistent with this behavior, the PP and PP-HA surfaces indicated up- and down-regulation of genes and proteins to confirm conversion to M2 phenotype, indicating immunomodulatory behavior of the PP and PP-HA structures.

At the start of the process, macrophages were harvested and allowed to expand for seven days, during which the media was exchanged with media containing macrophage colony-stimulating factor (MCSF). After seven days of macrophage expansion, the macrophages were plated and plated dropwise onto surfaces containing MCSF. Macrophage experiments were subsequently carried out. Specifically, two days after plating, the media was exchanged with fresh media and five test groups were assayed: porous PEEK (PP), porous PEEK with an HA coating (PP-HA), solid PEEK (SP), and two control groups treated with M1 and M2 treatment, respectively. No MCSF was provided to any of the test groups.

Figure 18:
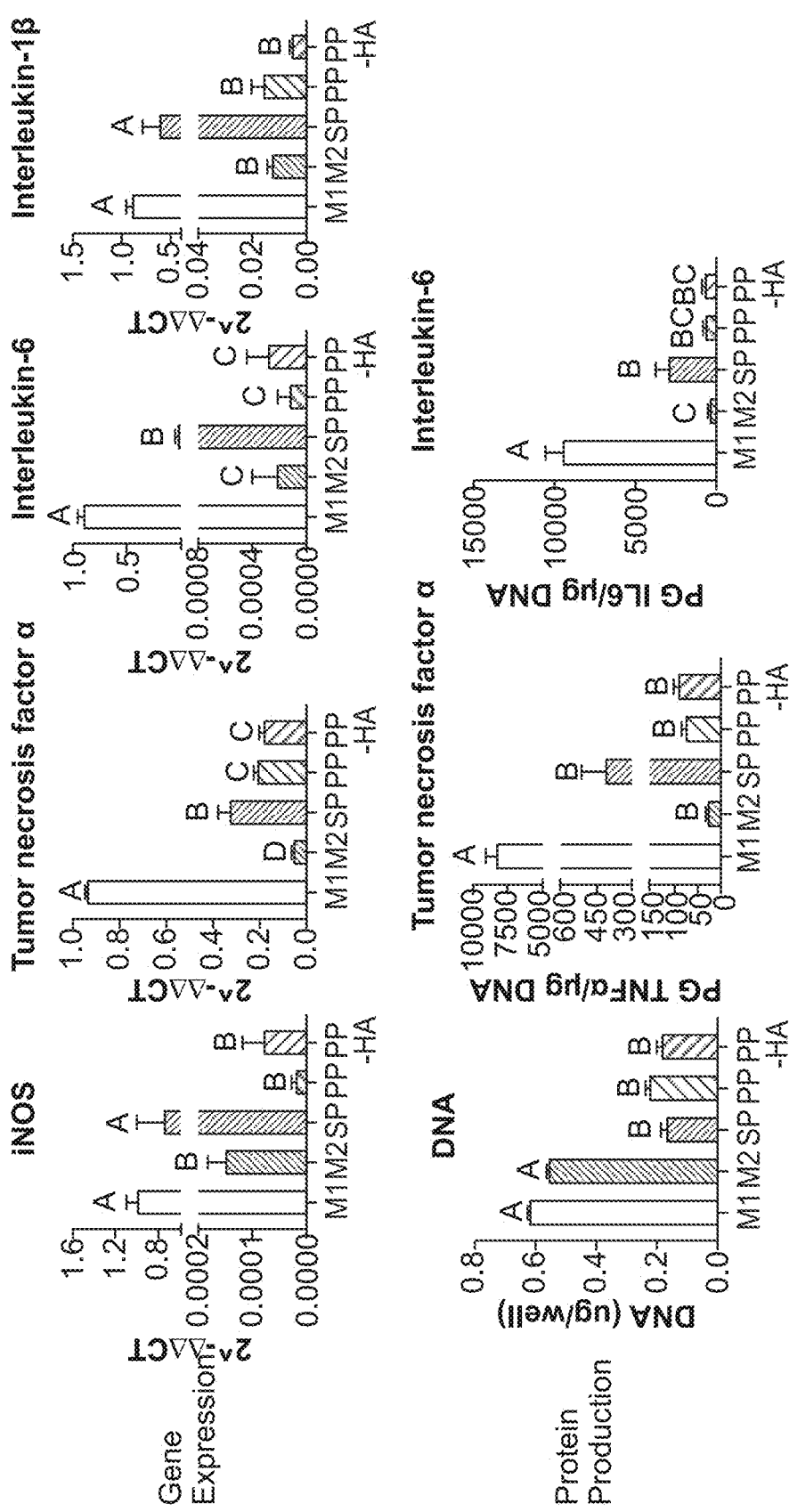
FIGS. 18-21 are plots of results of macrophage assays.
Figure 19:
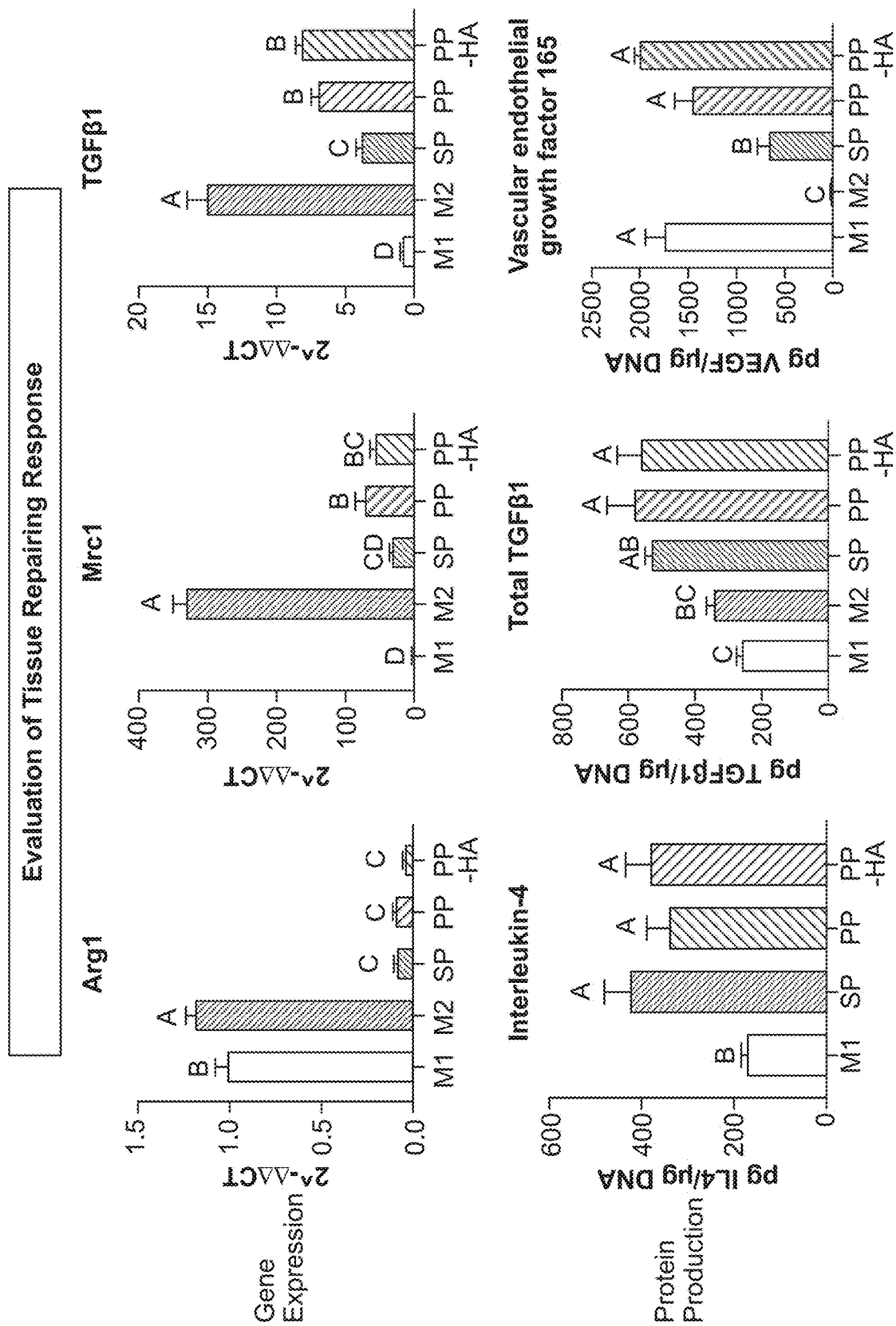
Figure 20:
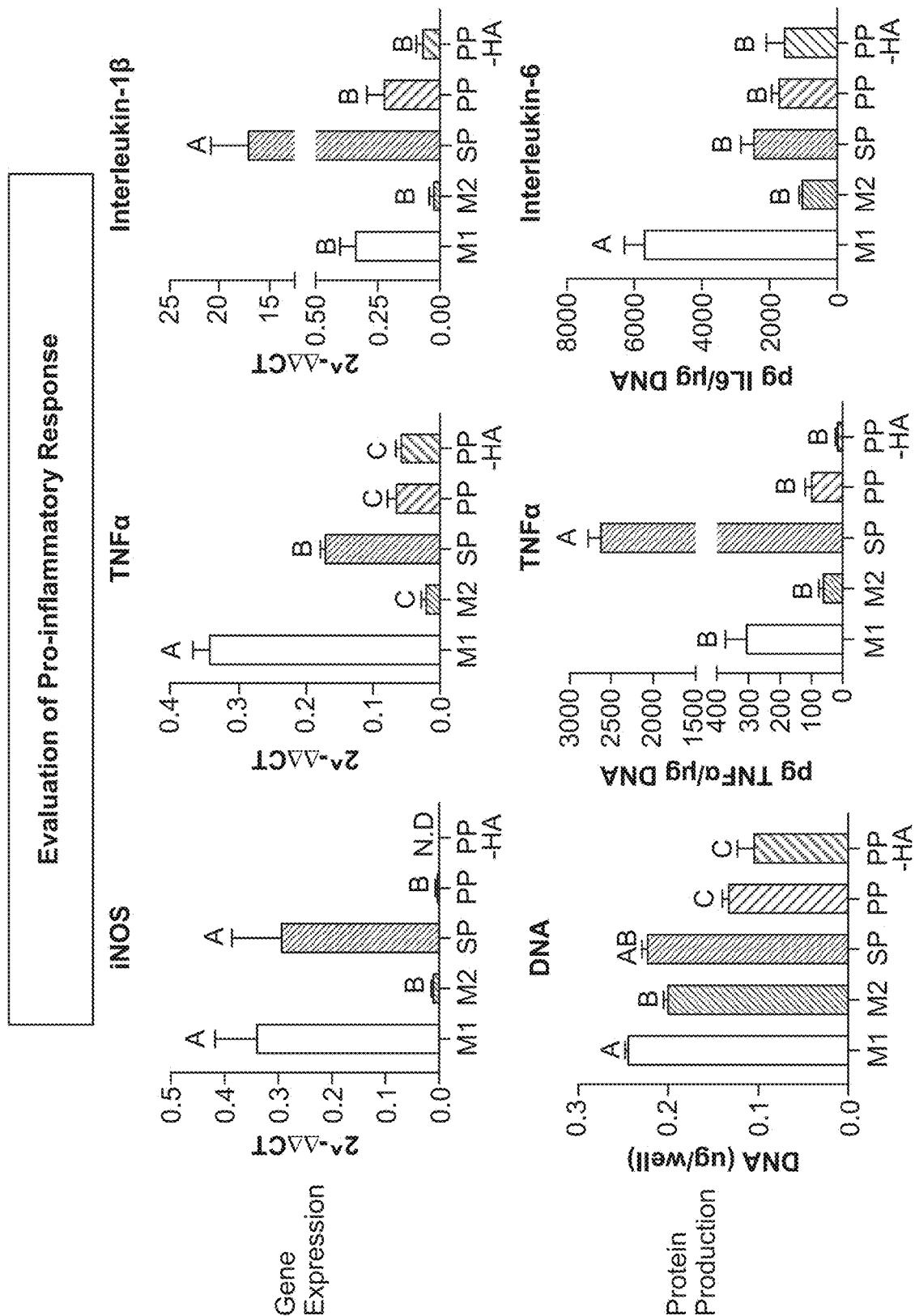
Figure 21:
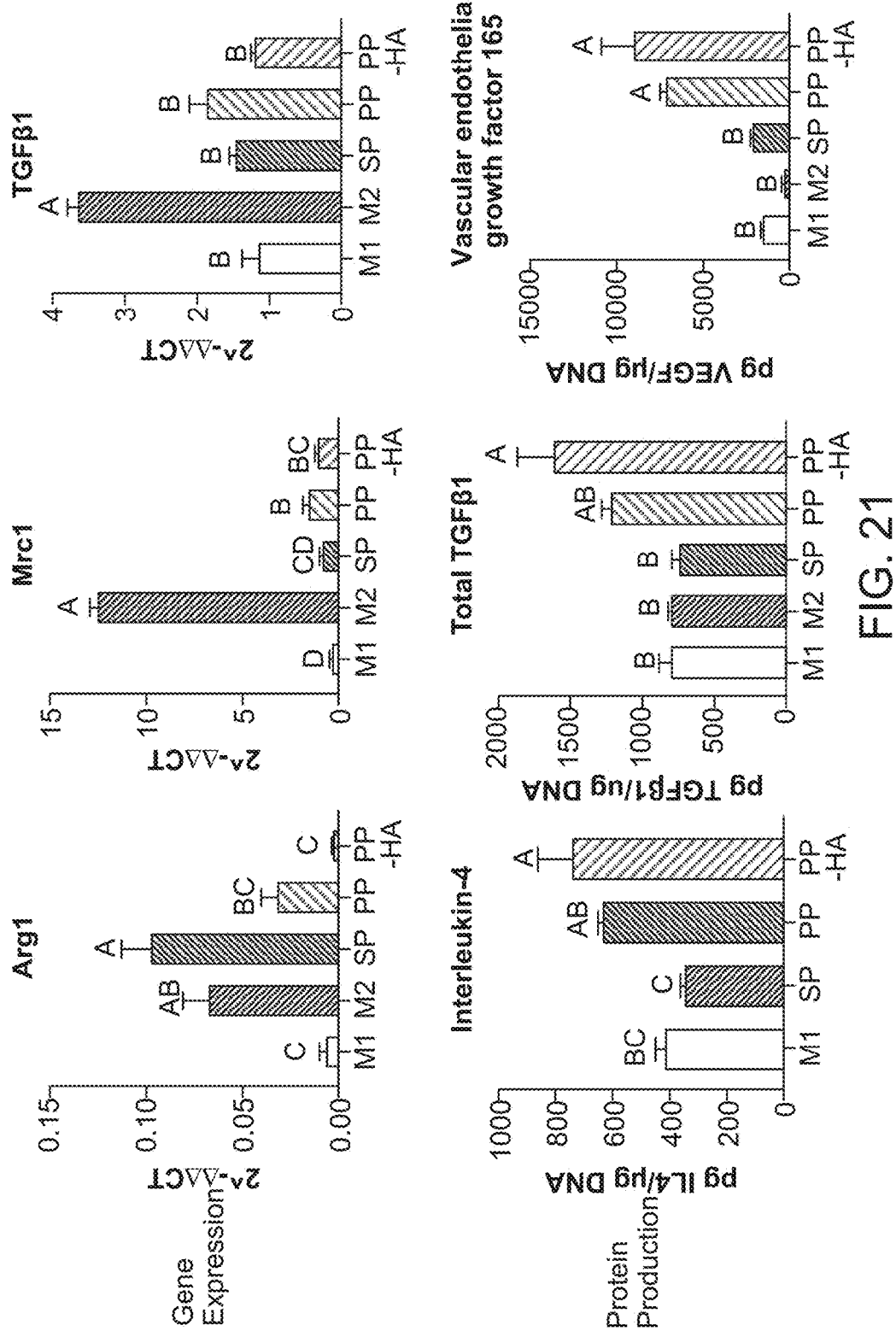

Results of assays indicative of pro-inflammatory response (e.g. M1 expression) are shown in FIG. 18, and indicate that porous PEEK suppresses the M1 inflammatory phase, particularly relative to solid PEEK. Results of assays indicative of tissue repairing response (e.g., M2 expression) are shown in FIG. 19, and indicate that porous PEEK facilitates M2 expression (pro-regenerative and leading to bone formation). Further assays were performed seven days after plating. These results are shown in FIGS. 20 and 21 and are generally consistent with the two-day results of FIGS. 18 and 19: porous PEEK suppresses the inflammatory phase and facilitates M2 expression.

These results demonstrate that the up- and down-regulation of genes and proteins by PP and PP-HA samples results in macrophage polarization to the pro-regenerative M2 phenotype, along with expected gene and protein expression/production. These results also demonstrate the suppression and downregulation of the pro-inflammatory genes and proteins of the M1 phenotype.

These results are generally consistent with the hBMSC assays discussed above: the PEEK samples show markers indicative of bone growth to a greater extent than do the control samples. Taken together, these validated, cellular assays confirm that porous PEEK and porous PEEK with an HA coating, fabricated according to the fused filament fabrication process described above, demonstrate both osteogenic potential and immunomodulation (immuno-osteogenesis), which is generally uncommon behavior for PEEK surfaces.

Notably, the assays described above favor materials that are known to be hydrophilic and physiologic (e.g., Ca/P chemistry), with sub-micron surface morphology, needle-like morphology, and sub-micron pore size. The porous PEEK implants described here have these features. Specifically, these results demonstrate that even porous PEEK implants without the HA coating have sufficient characteristics, e.g., imparted by the fused filament fabrication process, to provide positive results in these assays.

The foregoing osteogenesis experiments were conducted according to the following process. Human female MSCs (23 year old Caucasian) were cultured to confluence in MSC growth medium (GM) before plating onto test surfaces. Test discs from each group were placed in a 24-well plate at a density of 10,000 cells/cm$^2$ at 0.5 mL per well (20,000 cells/mL/well). Twenty-four hours after plating, the GM was changed, and subsequent GM changes were performed every 48 hours thereafter up to fourteen days. At the beginning of day fourteen, the media was replaced with fresh GM and cells were incubated for 24 hours before harvest. At harvest, media was collected and aliquoted into 1.5 mL Eppendorf centrifuge tubes. The wells with MSCs were rinsed twice with 1 mL of phosphate-buffered saline (PBS), placed in 0.5 mL of 0.05% Triton-X100, and frozen at −80° C. for biological assays.

To analyze DNA content, cell layers were lysed by ultrasonication at 40 V for 10 seconds/well and the total DNA content was determined by fluorescence. Protein and cytokine production levels in the conditioned media were quantified using enzyme-linked immunosorbent assays according to the manufacturer's protocol. Proteins analyzed included osteocalcin (OCN), osteoprotegerin (OPG), bone morphogenetic protein 2 (BMP2), bone morphogenetic protein 4 (BMP4), bone morphogenetic protein 7 (BMP7), interleukin 6 (IL6), interleukin 4 (IL4), and interleukin 10 (IL10).

The following experimental protocol was followed to characterize the macrophage polarization response to various implants using primary naïve bone marrow derived macrophages.

Naïve macrophages were cultured on TCPS, Porous PEEK (PP), Porous PEEK plus Hydroxy Apatite (PP-HA), and Solid PEEK (SP) 1 and 3 days in RPMI basal media supplemented with 10% fetal bovine serum (FBS), 1% penicillin/streptomycin Pen/Strep, and 30 ng/mL macrophage colony stimulating factor (M-CSF). These cultures were compared to M1 and M2 induced macrophage phenotypes. M1 was induced by supplementing growth media with interferon-γ (IFN-γ) and lipopolysaccharide (LPS), and M2 was induced using IL-4/IL-13. M1 and M2 induced macrophages were compared to naïve macrophages cultured on surface materials. Secreted inflammatory markers TNFα, IL-1, IL-4, IL-6, IL-10, IL-13 were quantified in response to implant materials. Gene expression was determined for inducible nitric oxide synthase (iNOS), a marker for the M1 phenotype, and arginine-1 (Arg1), a marker for the M2 phenotype.

The bone marrow harvest was performed as follows. Primary murine macrophages were isolated from the femurs of 6-8 week old male C57BL/6 mice. Bone marrow cells were flushed from the femurs of mice using Dulbecco's phosphate-buffered saline. Red blood cells were lysed from the bone marrow extract with ACK lysing buffer. Cells were collected and pooled to create a mixed population of murine cells. Cells were counted, and plated on 75 $cm^2$ at a density of 500,000 cells/mL in 10 mL RPMI 1640 media supplemented with 10% FBS, 50 U/mL penicillin-50 μg/mL streptomycin, and 30 ng/mL macrophage colony stimulating factor. Cells were cultured at 37° C., 5% CO2, and 100% humidity. Seven days after plating to create a homogenous naïve macrophage population, macrophages were passaged using Accutase and seeded on specified surfaces at a density of 20,000 cells/$cm^2$.

For surface plating, PP, PP-HA, and SP coupons were cleaned and gamma irradiated. Naïve macrophages were plated on surfaces in RPMI1640 culture medium with 30 ng/mL M-CSF and compared to M1 and M2 induced macrophage phenotypes plated on TCPS. M1 phenotype was induced by supplementing growth media with IFN-gamma (20 ng/mL) and LPS (100 ng/mL) at the time of plating. M2 was induced using IL-4/IL-13 (20 ng/ml of each) at the time of plating. Macrophages were plated on surfaces in 24-well plate at a density of 10,000 cells/$cm^2$ (20,000 cells/mL/well). RPMI 1640 with M-CSF was changed 24 hours before harvest.

After 24 hours of treatment, conditioned media was collected and aliquoted into 1.5 mL Eppendorf centrifuge tubes. The wells were rinsed twice with 1 mL of PBS and aspirated. 1 mL of 0.05% Triton-X was added and frozen at −20° C. overnight. Secreted inflammatory markers TNFα, IL113, IL4, IL6, IL10, and IL13 were quantified in response to surfaces utilizing ELISAs following the manufacturer's protocol. Immunoassay results were normalized to dsDNA content in cell lysates. Media was analyzed by ELISA according to manufacturing protocol.

For PCR harvest, cells were lysed and homogenized in QiaZol for isolation using spin columns. Cell monolayers were washed in PBS, lysed in 0.05% Triton X-100, and homogenized by sonication at 40V for 10 seconds/well. RNAeasy spin columns were run per manufacturer's instructions and quantified using the Take3 spectroscopy instrument (Qiagen). mRNA was measured for iNos (M1) and Arg1 (M2), and normalized to Gapdh.

Example 3: Live Animal Testing of Porous PEEK Implants

Various types of PEEK implants were implanted into aged female sheep (4-5 years old), including a porous PEEK implant, a porous PEEK implant with an HA coating, and a solid PEEK implant. Implants were 25 mm×6 mm outer diameter. Implants were evaluated with respect to bone outgrowth at the bone-implant interface at 4 and 12 weeks after surgery. Surface characterizations of the implants were performed prior to implantation using optical microscope and scanning electron microscopy. The cortical and cancellous implantation sites, and the mechanical properties of the implants in the cortical bone sites, were evaluated radiographically over time. New bone formation was evaluated over time based on routine PMMA histology in cortical and cancellous sites.

Implants were placed in the cancellous bone of the distal femur and proximal tibia in a press fit manner, and in the cortical bone of the tibia in a line-to-line manner. The samples were examined using standard shear stress push out testing as well as histological and morphological examinations at 4 and 12 weeks after surgery.

At the designated time point, each animal was euthanized and examined and dissected according to SOP-28. The right and left hind limbs were harvested, photographed, and radiographed. The tibia and femurs were scanned using a Siemens Inveon Micro CT to provide high resolution scans of the bone-implant interface as well as to assess any osseointegration. Cancellous sites were isolated and fixed in cold phosphate-buffered formaline. Cortical sites were isolated and sectional in the sagittal plane to isolate a medial and lateral specimen for push out testing.

Cortical and cancellous specimens were processed for PMMA histology immediately following isolation. Specimens were placed in 10% buffered formalin and sequentially dehydrated in increasing concentrations of ethanol for embedding in polymethylmethacrylate (PMMA) according to SOP-24. Embedded cortical and cancellous implants were sectioned along the long axis of the implant using a Leica SP 1600 Microtome according to SOP-35. A minimum of two thin (15-20 micron) sections were cut from each embedded implant and stained with methylene blue and basic fuschin, resulting in bone staining pink and fibrous tissue staining blue or purple.

Figure 22A:
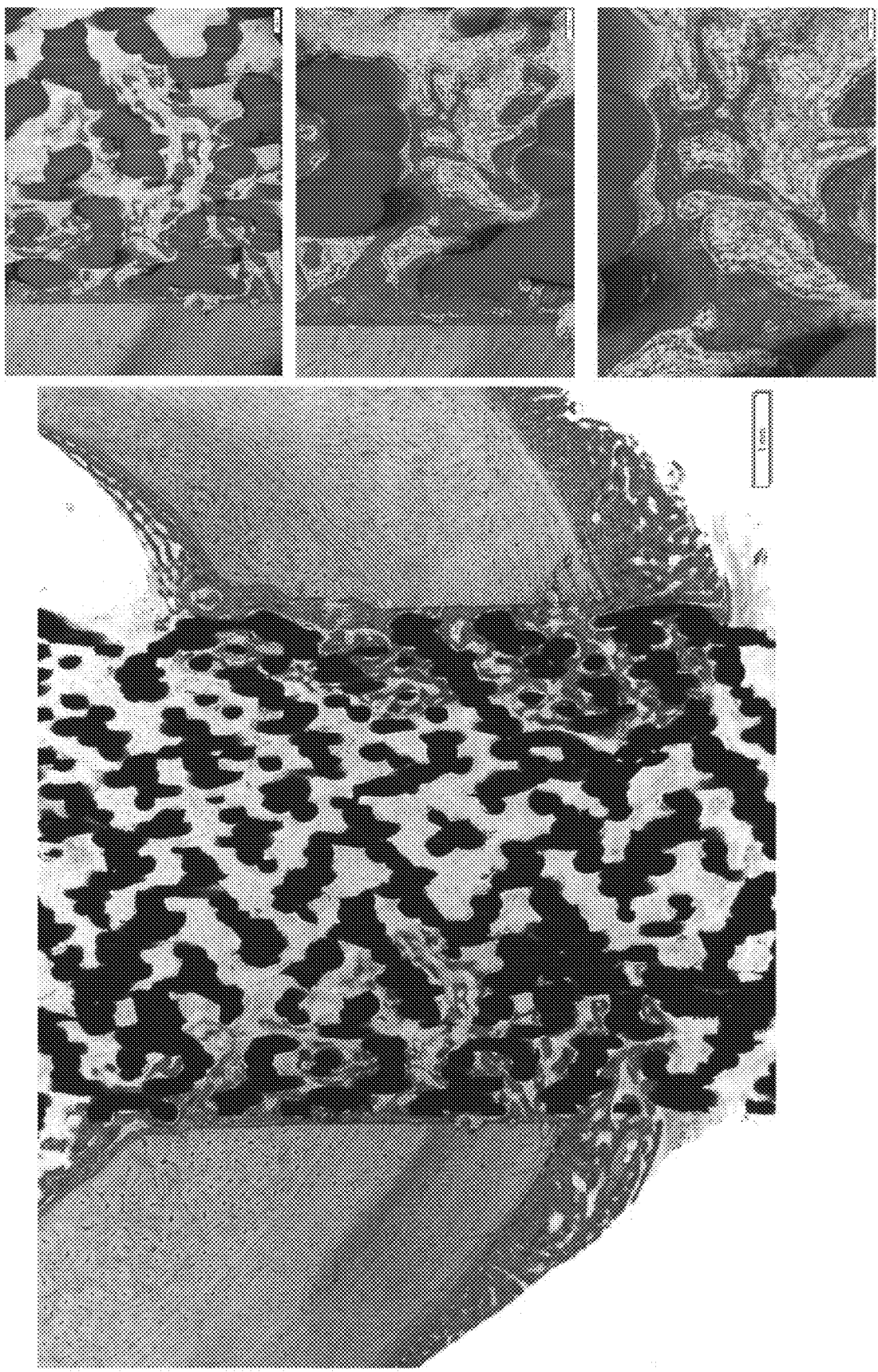
FIGS. 22A and 22B are images showing histology at 4 weeks after implantation of a porous PEEK implant with an HA coating.
Figure 22B:
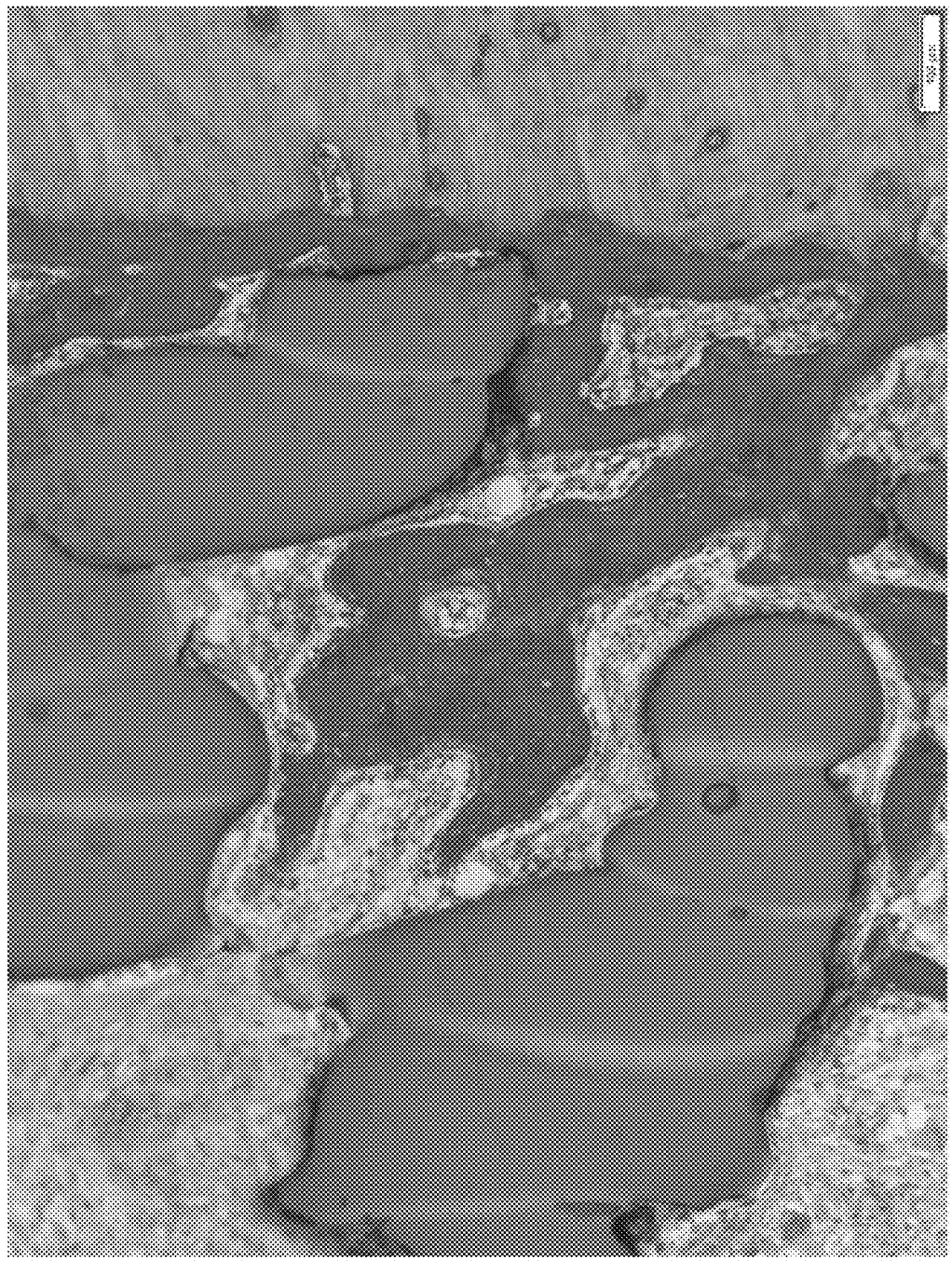
Figure 23:
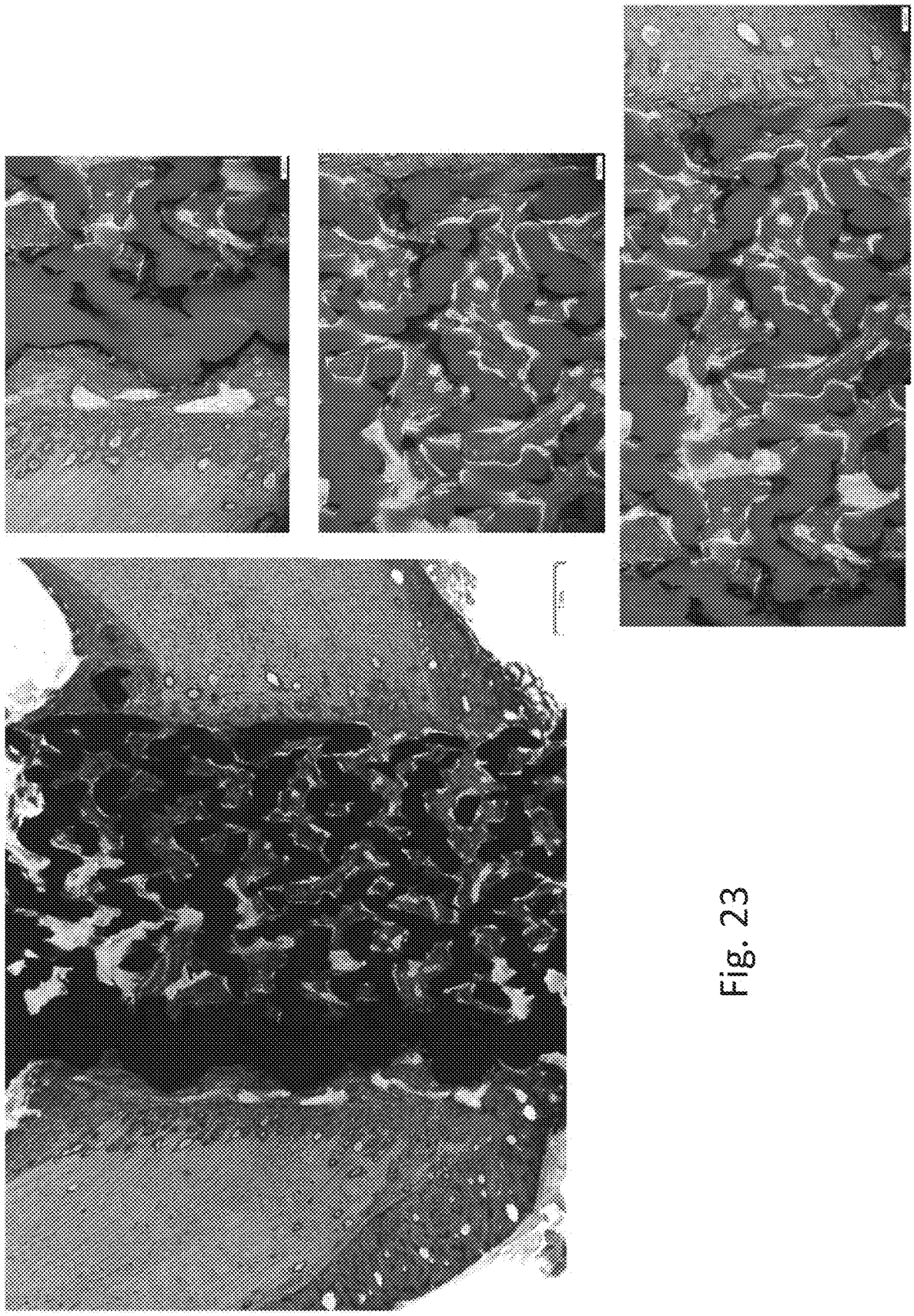
FIG. 23 is images showing histology at 12 weeks after implantation.

FIGS. 22A and 22B include images showing histology at 4 weeks after implantation of a porous PEEK implant with an HA coating. With reference specifically to FIG. 22B, lighter, translucent bands in the image of the implant indicate that the PEEK is amorphous, while the opaque regions are crystalline. FIG. 23 includes images showing histology at 12 weeks after implantation. These images show bone infiltration and osseointegration throughout the implant, demonstrating the effectiveness of the implant in promoting osteoconduction, osseointegration, and osteogenesis.

Figure 24:
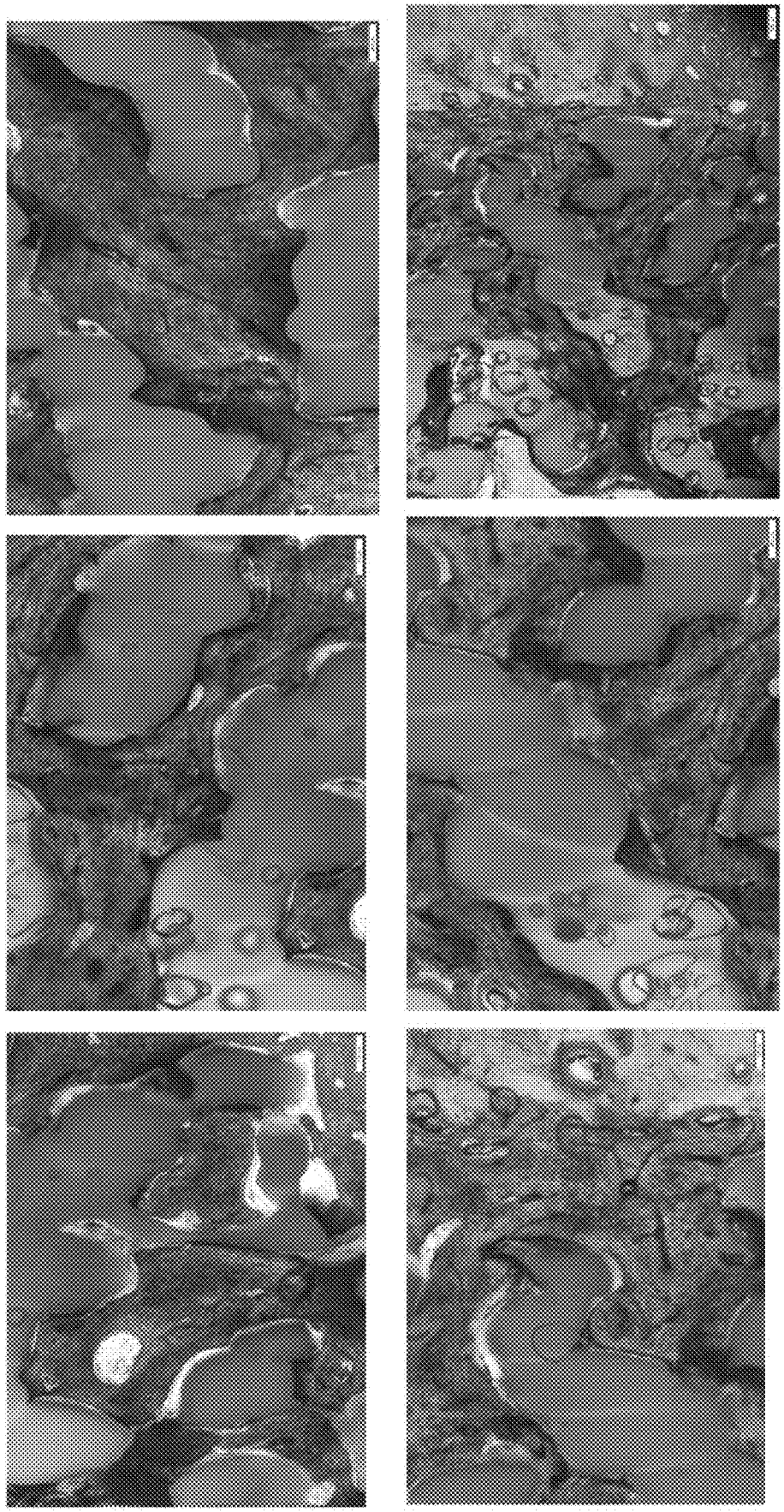
FIG. 24 is images showing histology at 12 weeks after implantation of a porous PEEK implant with an HA coating.

FIG. 24 includes additional images showing histology at 12 weeks after implantation of a porous PEEK implant with an HA coating. These images show the layering of the PEEK in the implant itself: lighter, translucent bands are amorphous regions, while opaque regions are crystalline. Cortical bone, which is generally stained purple, has grown through the implant without significant growth of fibrous tissue. Vessels are present, e.g., formed from epithelial cells and allowing supply of bone marrow, blood, etc. to the bone. Osteoblasts and osteocytes are also present, indicating healthy, new bone growth.

Figure 25A:
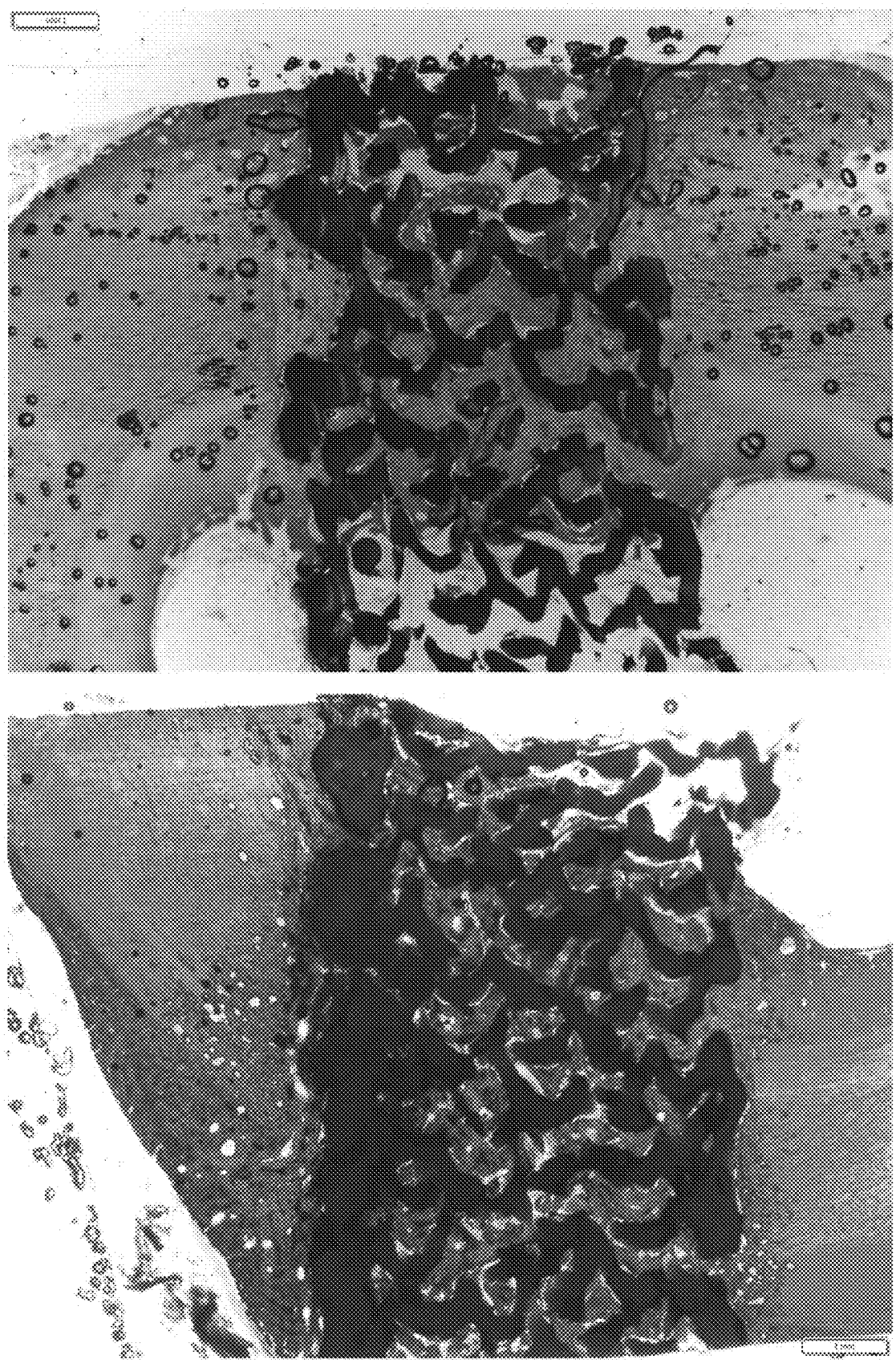
FIG. 25A is images showing histology at 12 weeks after implantation into different animals of a porous PEEK implant with an HA coating.
Figure 25B:
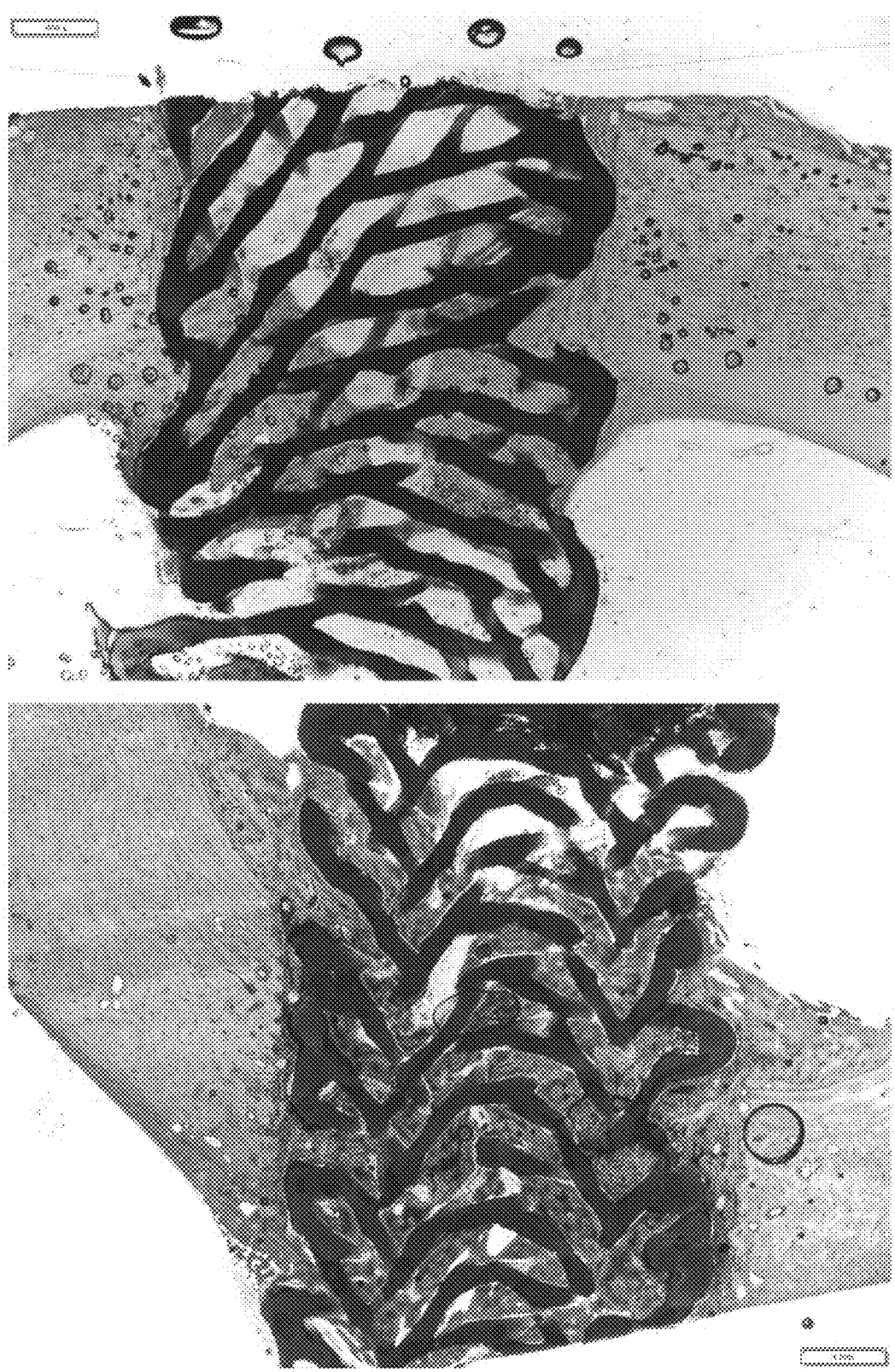
FIG. 25B is images showing histology at 12 weeks after implantation into different animals of a porous PEEK implant without HA coating.

FIGS. 25A and 25B include images showing histology at 12 weeks after implantation into different animals of a porous PEEK implant with an HA coating (FIG. 25A) and a porous PEEK implant without HA coating (FIG. 25B). These images show new bone growth throughout the porous structure of both implants.

Figure 26:
FIG. 26 is 12 week histology images of a porous PEEK implant without HA coating implanted at a metaphyseal site.

FIG. 26 is a 12 week histology image of a porous PEEK implant without HA coating implanted at a metaphyseal site.

This image shows cancellous bone growth throughout the porous structure of the implant.

Figure 27:
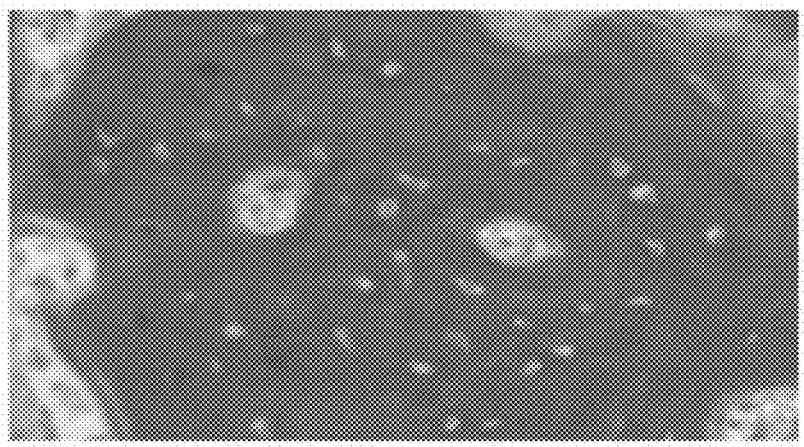
FIG. 27 is transmitted light images of 12 week histology of porous PAEK implants from sheep.
Figure 27:
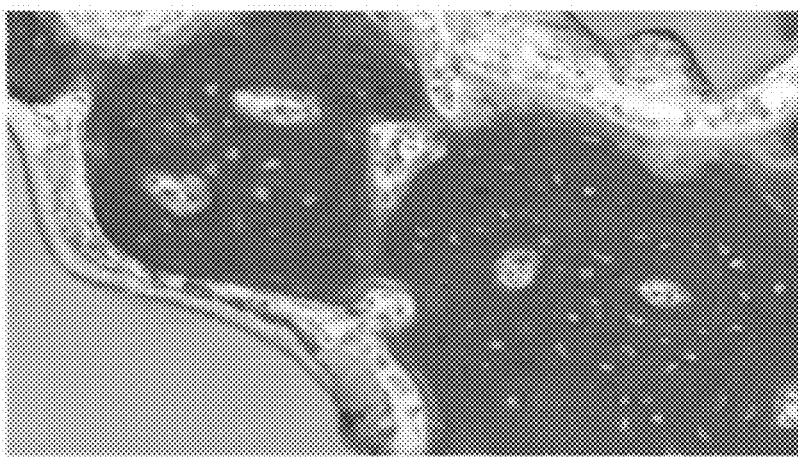
Figure 28:
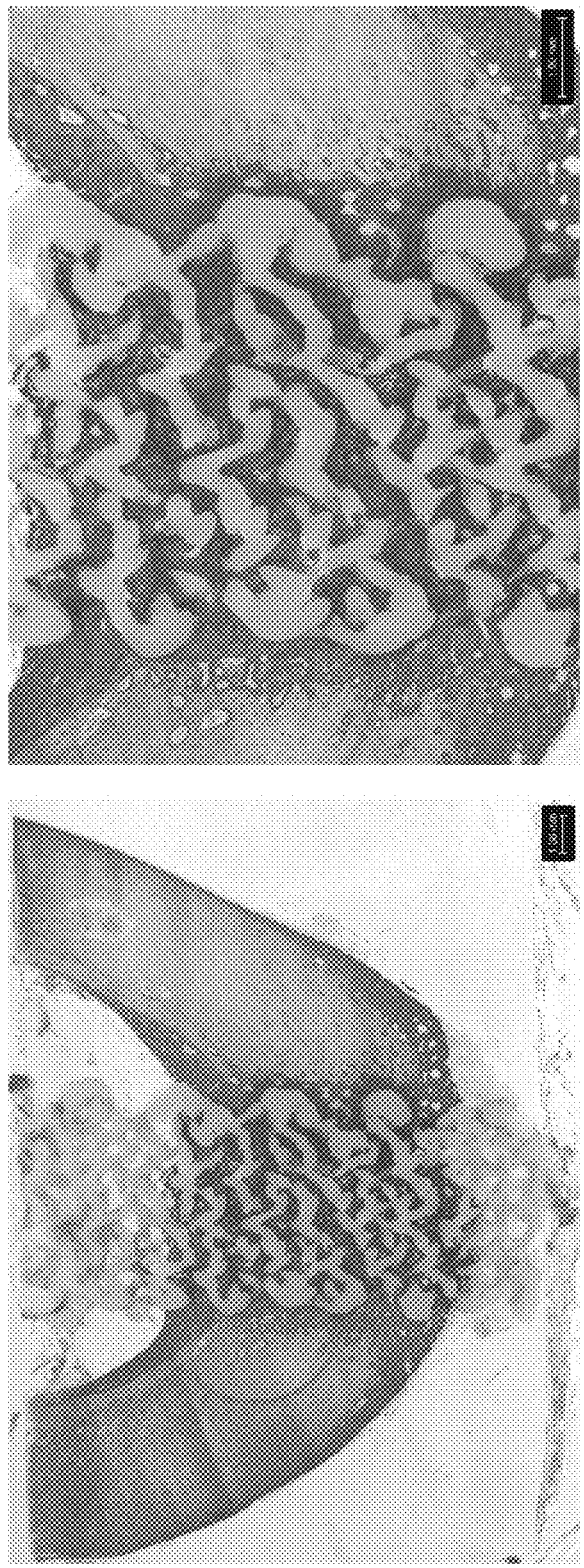
FIG. 28 is stereomicroscope images of 12 week histology of porous PAEK implants from sheep.
Figure 28:
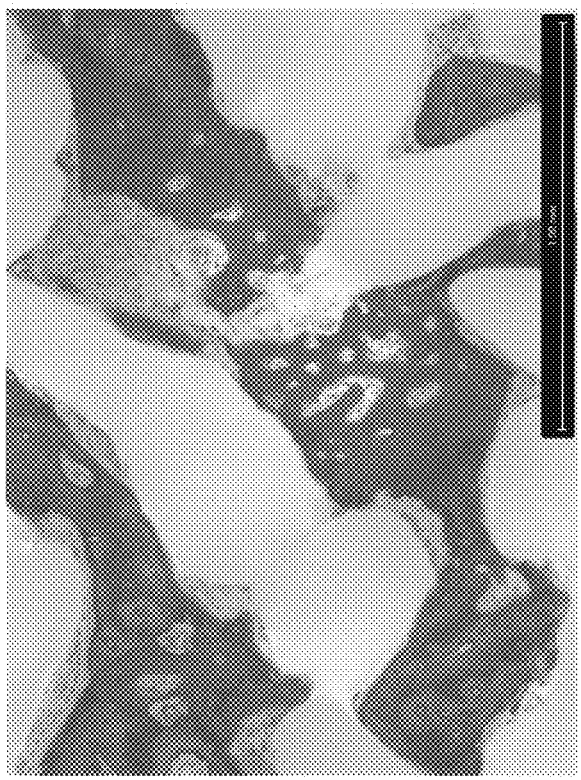

FIGS. 27-28 are 12 week histology images of porous PAEK implants from sheep, illustrating the quality of bone formation in the implants. FIG. 27 includes transmitted light images and FIG. 28 includes stereomicroscope images. These images demonstrate the formation of bone structure in the implant, such as blood vessels, osteocytes, circular osteon formation.

Figure 29:
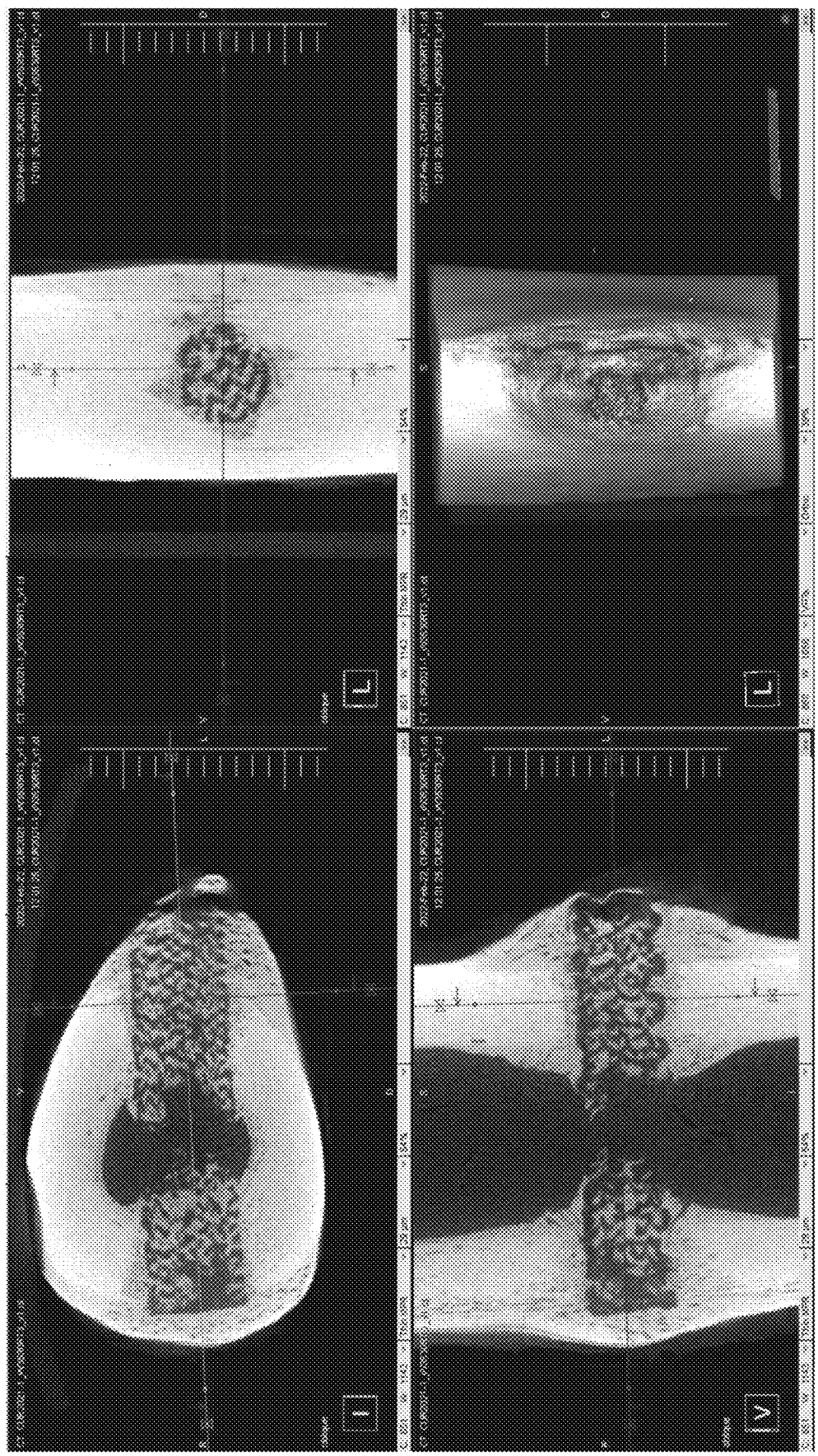
FIG. 29 includes micro-computed tomography images.

FIG. 29 are micro-computed tomography (micro-CT) images taken 12 weeks after implantation of a porous PEEK implant with an HA coating. These images demonstrate bone growth around and through the implant. For instance, the lateral and medial side of the bone, where a drill hole had been created to insert the implant, show healing bone growth. Specifically, white areas, e.g., region 60, are original cortical bone, while gray regions, e.g., region 62, are new bone growth. These images also show bone growing throughout the pores of the implant: the implant is dark and the bone, which pervades the porous structure of the implant, is white.

In embodiment 1, an article includes multiple layers of polyaryletherketone (PAEK), in which each layer is composed of a continuous length of PAEK, in which the continuous length of PAEK in at least one of the layers includes: an interior portion, and an exterior surface including crystalline regions, in which a crystallinity of the exterior surface is higher than a crystallinity of the interior portion. The cross-sectional area of the continuous length of PAEK is non-uniform within each layer, or each layer defines a plane and a portion of the continuous length of PAEK in each layer extends out of the plane defined by the layer, or both. The multiple layers of PAEK define a network of interconnected pores.

In embodiment 2, combinable with embodiment 1, the continuous length of PAEK in each layer is disposed in aligned rows.

In embodiment 3, combinable with embodiment 2, the rows have a serpentine, curved, or zig-zag configuration.

In embodiment 4, combinable with any of embodiments 2 or 3, the rows in each layer are rotated relative to the rows in an adjacent layer.

In embodiment 5, combinable with embodiment 4, the rows in each layer are rotated by between 20-60° relative to the rows in the adjacent layer.

In embodiment 6, combinable with embodiment 5, the rows in each layer are rotated by 36° relative to the rows in the adjacent layer.

In embodiment 7, combinable with any of the preceding embodiments, the cross sectional area of the continuous length of PAEK is non-uniform within each layer.

In embodiment 8, combinable with any of the preceding embodiments, the continuous length of PAEK is extends between adjacent layers.

In embodiment 9, combinable with any of the preceding embodiments, each layer defines a plane, and in which a portion of the continuous length of PAEK in each layer extends out of the plane defined by the layer.

In embodiment 10, combinable with any of the preceding embodiments, the continuous length of PAEK in each layer intersects the continuous length of PAEK in an adjacent layer at nodes.

In embodiment 11, combinable with embodiment 10, the continuous length of PAEK extending between adjacent nodes is non-linear.

In embodiment 12, combinable with any of the preceding embodiments, the exterior surface of the continuous length of PAAK includes crystalline domains separated by amorphous regions.

In embodiment 13, combinable with any of the preceding embodiments, the exterior surface of the continuous length of PAEK includes a lamellar surface microstructure.

In embodiment 14, combinable with embodiment 13, the lamellar surface microstructure has a characteristic dimension of between 4-6 nm.

In embodiment 15, combinable with embodiment 14, the lamellar surface microstructure forms spherules on the exterior surface of the continuous length of PAEK.

In embodiment 16, combinable with embodiment 15, the spherules have a characteristic dimension of 4-6 μm In embodiment 17, combinable with any of the preceding embodiments, the continuous length of PAEK in a first set layers of the multiple layers has a crystallinity that differs from the continuous length of PAEK in a second set of the layers of the multiple layers.

In embodiment 18, combinable with any of the preceding embodiments, the multiple layers of PAEK define a trabecular structure.

In embodiment 19, combinable with any of the preceding embodiments, the multiple layers of PAEK form a triply periodic minimal surface (TPMS) structure defining the network of interconnected pores.

In embodiment 20, combinable with embodiment 19, the multiple layers of PAEK form a TPMS diamond structure.

In embodiment 21, combinable with any of the preceding embodiments, a surface roughness of the continuous length of PAEK is between 0.5 μm and 3.0 μm.

In embodiment 22, combinable with embodiment 21, the surface roughness of the continuous length of PAEK is between 1 μm and 1.5 μm.

In embodiment 23, combinable with any of the preceding embodiments, a Young's modulus of elasticity of the article is between 0.3 GPa and 4.0 GPa.

In embodiment 24, combinable with embodiment 23, the Young's modulus of elasticity of the article is between 0.8 GPa and 1.5 GPa.

In embodiment 25, combinable with any of the preceding embodiments, a compression strength of the article is at least 20 kN.

In embodiment 26, combinable with embodiment 25, the compression strength of the article is between 20 kN and 150 kN.

In embodiment 27, combinable with embodiment 26, the compression strength of the article is between 20 kN and 100 kN.

In embodiment 28, combinable with embodiment 27, the compression strength of the article is between 20 kN and 30 kN.

In embodiment 29, combinable with any of the preceding embodiments, a fatigue strength of the article is between 1200 N and 1800 N measured over 5 M cycles at 5 Hz.

In embodiment 30, combinable with any of the preceding embodiments, a stiffness of the article is between 0.8 GPa and 1.5 GPa.

In embodiment 31, combinable with any of the preceding embodiments, the article includes a coating including hydroxyapatite disposed on the exterior surface of the continuous length of PAEK.

In embodiment 32, combinable with embodiment 31, the coating has a thickness of between 1 nm and 80 nm.

In embodiment 33, combinable with embodiment 32, the coating has a thickness of between 1 nm and 50 nm.

In embodiment 34, combinable with embodiment 33, the coating has a thickness of between 1 nm and 20 nm.

In embodiment 35, combinable with any of the preceding embodiments, the continuous length of PAEK has between 20% and 60% crystallinity by volume.

In embodiment 36, combinable with embodiment 35, the continuous length of PAEK has between 30% and 50% crystallinity by volume.

In embodiment 37, combinable with any of the preceding embodiments, the article has a porosity of between 40-80%.

In embodiment 38, combinable with any of the preceding embodiments, the pores have dimensions between 100 μm-1 mm.

In embodiment 39, combinable with embodiment 38, the pores have dimensions between 100 μm and 700 μm.

In embodiment 40, combinable with any of the preceding embodiments, an average dimension of the pores is between 220-280 μm.

In embodiment 41, combinable with any of the preceding embodiments, the PAEK includes polyetheretherketone (PEEK).

In embodiment 42, combinable with any of the preceding embodiments, the multiple layers of PAEK define a first region having a first porosity and a second region having a second porosity different from the first porosity, and both the first region and the second region span at least some of the multiple layers.

In embodiment 43, combinable with embodiment 42, the continuous length of PAEK extends between the first region and the second region.

In embodiment 44, combinable with any of the preceding embodiments, the continuous length of PAEK is deposited by additive manufacturing.

In embodiment 45, combinable with embodiment 44, the continuous length of PAEK is deposited by fused strand fabrication.

In embodiment 46, combinable with any of the preceding embodiments, the article includes a medical implant.

In embodiment 47, combinable with embodiment 46, the medical implant is osteoconductive.

In embodiment 48, combinable with any of embodiments 46 to 47, the medical implant is osteointegrative.

In embodiment 49, combinable with any of embodiments 46 to 48, the medical implant is osteogenic.

In embodiment 51, a medical implant includes multiple layers of PAEK deposited by fused strand fabrication, in which each layer is composed of a continuous length of PAEK disposed in aligned rows, and in which the continuous length of PAEK extends between adjacent layers, in which the continuous length of PAEK in at least one of the layers includes: an interior portion, and an exterior surface including crystalline regions, in which a crystallinity of the exterior surface is higher than a crystallinity of the interior portion, and the cross-sectional area of the continuous length of PAEK is non-uniform within each row; in which the rows in each layer are rotated relative to the rows in each adjacent layer to form a TPMS diamond structure defining a network of interconnected pores such that a porosity of the medical implant is between 50-70%, and in which the medical implant is osteoconductive.

In embodiment 52, combinable with embodiment 51, the medical implant includes a cervical implant.

In embodiment 53, combinable with any of embodiments 51 to 52, the medical implant includes a posterior lumbar interbody fusion implant, a transforaminal lumbar interbody fusion implant, an anterior lumbar interbody fusion implant, or a direct lateral interbody fusion implant.

In embodiment 54, combinable with any of embodiments 51 to 53, the medical implant includes a joint implant.

In embodiment 55, a medical implant is produced by a process including:
extruding a filament of PAEK from a nozzle of an additive manufacturing tool to deposit each of multiple layers of PAEK, in which each layer is composed of a continuous length of PAEK; and
annealing the deposited multiple layers to induce crystallization of regions of an exterior surface of the continuous length of PAEK, in which a crystallinity of the exterior surface is higher than a crystallinity of an interior portion of the continuous length of PAEK,
in which the multiple layers of PAEK define a network of interconnected pores.

In embodiment 56, combinable with embodiment 55, the process includes extruding the filament of PAEK includes forming aligned rows of the continuous length of PAEK in each layer.

In embodiment 57, combinable with any of embodiments 55 to 56, the process includes continuously extruding the filament of PAEK to form adjacent layers such that the continuous length of PAEK extends between the adjacent layers.

In embodiment 58, combinable with any of embodiments 55 to 57, the process includes extruding the filament of PAEK such that each layer defines a plane, and such that a portion of the continuous length of PAEK extends out of the plane defined by the layer.

In embodiment 59, combinable with any of embodiments 55 to 58, the process includes extruding the filament of PAEK such that the continuous length of PAEK in each layer intersects that continuous length of PAEK in an adjacent layer at nodes.

In embodiment 60, combinable with embodiment 59, the continuous length of PAEK extending between adjacent nodes is non-linear.

In embodiment 61, combinable with any of embodiments 55 to 60, the process includes extruding the filament of PAEK such that the continuous length of PAEK has a non-uniform cross-sectional area within each layer.

In embodiment 62, combinable with any of embodiments 55 to 61, the process includes extruding the filament of PAEK such that the multiple layers form a triply periodic minimal surface (TPMS) structure defining the network of interconnected pores.

In embodiment 63, combinable with embodiment 62, the multiple layers form a TPMS diamond structure.

In embodiment 64, combinable with any of embodiments 55 to 63, the process includes rotating the additive manufacturing tool after depositing each layer of PAEK.

In embodiment 65, combinable with embodiment 64, the process includes rotating the additive manufacturing tool by between 20-60° after depositing each layer.

In embodiment 66, combinable with any of embodiments 55 to 65, the process includes heating the nozzle of the manufacturing tool to a temperature of between 325-475° C.

In embodiment 67, combinable with embodiment 66, the process includes heating the nozzle to a temperature of between 400-450° C.

In embodiment 68, combinable with any of embodiments 55 to 67, extruding the filament of PAEK includes depositing a first one of the layers onto a heated platform.

In embodiment 69, combinable with any of embodiments 55 to 68, the process includes extruding the filament of PAEK at an extrusion flow rate of between 10-15 mm/s.

In embodiment 70, combinable with any of embodiments 55 to 69, the process includes moving the nozzle relative to the deposited layers at a feed rate of between 5-15 mm/s.

In embodiment 71, combinable with any of embodiments 55 to 57, the process includes extruding the filament of PAEK at an extrusion ratio of between 0.5-4.0, the extrusion ratio is the ratio between an extrusion flow rate of the PAEK to a rate of motion of the nozzle relative to the deposited layers.

In embodiment 72, combinable with embodiment 71, including extruding the filament of PAEK at an extrusion ratio of between 0.5-2.0.

In embodiment 73, combinable with embodiment 72, including extruding the filament of PAEK at an extrusion ratio of between 0.6-1.0.

In embodiment 74, combinable with any of embodiments 55 to 73, the process includes annealing the deposited multiple layers at a temperature below a glass transition temperature of the PAEK.

In embodiment 75, combinable with embodiment 74, annealing the deposited multiple layers includes forming a lamellar surface microstructure on the exterior surface of the continuous length of PAEK.

In embodiment 76, combinable with any of embodiments 55 to 75, the process includes disposing a coating including hydroxyapatite onto the exterior surface of the continuous length of PAEK.

In embodiment 77, combinable with embodiment 76, disposing the coating includes disposing the coating by dip coating, immersion coating, or spray coating.

In embodiment 78, combinable with any of embodiments 55 to 77, the process includes extruding the filament of PAEK using a fused strand deposition process.

In embodiment 79, combinable with any of embodiments 55 to 77, the process includes extruding the filament of PAEK using a fused filament fabrication process.

In embodiment 80, combinable with any of embodiments 55 to 77, the process includes extruding the filament of PAEK using a fused melt deposition process.

In embodiment 81, combinable with any of embodiments 55 to 80, the process includes extruding the filament of PAEK to form a first region having a first porosity and a second region having a second porosity different from the first porosity, in which both the first region and the second region span at least some of the multiple layers.

In embodiment 82, combinable with embodiment 81, the continuous length of PAEK extends between the first region and the second region.

Particular embodiments of the subject matter have been described. Other embodiments are within the scope of the following claims.

What is claimed is:

1. An article comprising:
   multiple layers of polyaryletherketone (PAEK), in which each layer is composed of a continuous strand of PAEK, in which the continuous strand of PAEK in at least one of the layers comprises:
   an interior portion, and
   an exterior surface including crystalline regions, in which a crystallinity of the exterior surface is higher than a crystallinity of the interior portion;
   in which the cross-sectional area of the continuous strand of PAEK is non-uniform within each layer, and
   in which the multiple layers of PAEK define a network of interconnected pores.

2. The article of claim 1, in which the continuous strand of PAEK in each layer is disposed in aligned rows, and in which the rows in each layer are rotated relative to the rows in an adjacent layer.

3. The article of claim 2, in which the rows in each layer are rotated by between 20-60° relative to the rows in the adjacent layer.

4. The article of claim 1, in which the continuous strand of PAEK extends between adjacent layers.

5. The article of claim 1, in which each layer defines a plane, and in which a portion of the continuous strand of PAEK in each layer extends out of the plane defined by the layer.

6. The article of claim 1, in which the continuous strand of PAEK in each layer intersects the continuous strand of PAEK in an adjacent layer at nodes, and in which the continuous strand of PAEK extending between adjacent nodes is non-linear.

7. The article of claim 1, in which the exterior surface of the continuous strand of PAEK comprises crystalline domains separated by amorphous regions.

8. The article of claim 1, in which the exterior surface of the continuous strand of PAEK comprises a lamellar surface microstructure, in which the lamellar surface microstructure has a characteristic dimension of between 4-6 nm.

9. The article of claim 8, in which the lamellar surface microstructure forms spherules on the exterior surface of the continuous strand of PAEK, in which the spherules have a characteristic dimension of 4-6 µm.

10. The article of claim 1, in which the continuous strand of PAEK in a first set of layers of the multiple layers has a crystallinity that differs from the continuous strand of PAEK in a second set of the layers of the multiple layers.

11. The article of claim 1, in which the multiple layers of PAEK define a trabecular structure.

12. The article of claim 1, in which the multiple layers of PAEK form a triply periodic minimal surface (TPMS) structure defining the network of interconnected pores.

13. The article of claim 1, in which a surface roughness of the continuous strand of PAEK is between 0.5 µm and 3.0 µm.

14. The article of claim 1, in which a Young's modulus of elasticity of the article is between 0.3 GPa and 4.0 GPa.

15. The article of claim 1, in which a compression strength of the article is at least 20 kN.

16. The article of claim 1, in which a fatigue strength of the article is between 1200 N and 1800 N measured over 5 M cycles at 5 Hz.

17. The article of claim 1, in which the continuous strand of PAEK has between 20% and 60% crystallinity by volume.

18. The article of claim 1, in which the article has a porosity of between 40-80%.

19. The article of claim 1, in which the article comprises a medical implant, and in which the medical implant is osteoconductive.

20. The article of claim 1, in which the article comprises a medical implant, and in which the medical implant is osteointegrative.

21. The article of claim 1, in which the article comprises a medical implant, and in which the medical implant is osteogenic.

22. The article of claim 21, in which a surface microstructure of the article contributes to osteogenicity of the article.

23. The article of claim 1, in which an opening is defined through the article, the opening extending from a first surface of the article to an opposing second surface, and in which the article comprises multiple radiographic markers, each marker extending from the first surface to the second surface of the article.

24. A method comprising:

implanting, in a patient, an article comprising:
multiple layers of polyaryletherketone (PAEK), in which each layer is composed of a continuous strand of PAEK, in which the continuous strand of PAEK in at least one of the layers comprises:
an interior portion, and
an exterior surface including crystalline regions, in which a crystallinity of the exterior surface is higher than a crystallinity of the interior portion;
in which the cross-sectional area of the continuous strand of PAEK is non-uniform within each layer, and
in which the multiple layers of PAEK define a network of interconnected pores.

25. The method of claim 24, in which the implanted article is osteogenic.

26. The method of claim 25, in which a surface microstructure of the article contributes to osteogenicity of the article.

27. The method of claim 24, in which a lamellar surface microstructure of the continuous strands of PAEK and a trabecular structure of the multiple layers of PAEK enable bone cells to enter and grow within the implanted article.

28. The article of claim 1, in which an average dimension of the pores is between 50 μm and 1 mm.

29. The article of claim 28, in which an average dimension of the pores is between 220 μm and 280 μm.

30. The article of claim 12, in which the multiple layers of PAEK form a TPMS diamond structure defining the network of interconnected pores.

* * * * *